US008628977B2

(12) United States Patent
Adamec et al.

(10) Patent No.: US 8,628,977 B2
(45) Date of Patent: Jan. 14, 2014

(54) GROUP SPECIFIC INTERNAL STANDARD TECHNOLOGY (GSIST) FOR SIMULTANEOUS IDENTIFICATION AND QUANTIFICATION OF SMALL MOLECULES

(75) Inventors: Jiri Adamec, West Lafayette, IN (US); Wen-Chu Yang, West Lafayette, IN (US); Fred E. Regnier, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 387 days.

(21) Appl. No.: 12/990,560

(22) PCT Filed: May 1, 2009

(86) PCT No.: PCT/US2009/002711
§ 371 (c)(1),
(2), (4) Date: Apr. 13, 2011

(87) PCT Pub. No.: WO2009/134439
PCT Pub. Date: Nov. 5, 2009

(65) Prior Publication Data
US 2011/0183430 A1    Jul. 28, 2011

Related U.S. Application Data

(60) Provisional application No. 61/126,235, filed on May 2, 2008.

(51) Int. Cl.
*G01N 24/00* (2006.01)
(52) U.S. Cl.
USPC ............... 436/173; 436/8; 436/56; 436/87; 436/89; 436/94; 436/106

(58) Field of Classification Search
None
See application file for complete search history.

(56) References Cited

U.S. PATENT DOCUMENTS

| 6,864,099 B2 | 3/2005 | Regnier |
| 6,872,575 B2 | 3/2005 | Regnier |
| 7,045,296 B2 | 5/2006 | Parker et al. |
| 7,982,070 B2 | 7/2011 | Smith et al. |

(Continued)

FOREIGN PATENT DOCUMENTS

| WO | WO 2007/109292 A2 | 9/2007 |
| WO | WO 2007/117665 A2 | 10/2007 |

(Continued)

OTHER PUBLICATIONS

Adamec, et al., "Development of a new method for improved identification and relative quantification of unknown metabolites in complex samples: determination of a triterpenoid metabolic fingerprint for the in situ characterization of *Ganoderma* bioactive compounds," Dec. 2009 *J. Pept. Sci.* 32:4052-4058.

(Continued)

*Primary Examiner* — Robert Xu
(74) *Attorney, Agent, or Firm* — Brown Rudnick LLP; Adam M. Schoen

(57) ABSTRACT

Reagents and methods are provided that permit simultaneous analysis of multiple diverse small molecule analytes present in a complex mixture. Samples are labeled with chemically identical but isotopically distinct forms of the labeling reagent, and analyzed using mass spectrometry. A single reagent simultaneously derivatizes multiple small molecule analytes having different reactive functional groups.

8 Claims, 7 Drawing Sheets

(56) References Cited

U.S. PATENT DOCUMENTS

| | | | |
|---|---|---|---|
| 2003/0186326 | A1 | 10/2003 | Regnier et al. |
| 2005/0148087 | A1 | 7/2005 | Pappin et al. |
| 2007/0099304 | A1 | 5/2007 | Puente et al. |
| 2007/0231827 | A1 | 10/2007 | Zhang |
| 2008/0050827 | A1 | 2/2008 | Mirzaei et al. |
| 2008/0050833 | A1* | 2/2008 | Smith et al. ............... 436/86 |
| 2010/0240137 | A1 | 9/2010 | Regnier |

FOREIGN PATENT DOCUMENTS

| | | | |
|---|---|---|---|
| WO | WO 2007/109292 | A3 | 5/2008 |
| WO | WO 2007/117665 | A3 | 5/2009 |
| WO | WO 2009/134439 | A2 | 11/2009 |
| WO | WO 2009/134439 | A3 | 3/2010 |

OTHER PUBLICATIONS

Bajad et al., "Separation and quantitation of water soluble cellular metabolites by hydrophilic interaction chromatography-tandem mass spectrometry," *J. Chromatogr. A.*, Aug. 25, 2006; 1125(1): 76-88. Available online Jun. 6, 2006.

Baxter et al., "Reductive Aminations of Carbonyl Compounds with Borohydride and Borane Reducing Agents," in *Organic Reactions vol. 59*, Wiley, New York, New York, 2002, pp. 1-714.

Bhattacharya et al., "Single-run separation and detection of multiple metabolic intermediates by anion-exchange high-performance liquid chromatography and application to cell pool extracts prepared from *Escherichia coli*," *Anal. Biochem.*, Nov. 20, 1995; 232(1): 98-106.

Buchholz et al., "Quantification of Intracellular Metabolites in *Escherichia coli* K12 Using Liquid Chromatographic-Electrospray Ionization Tandem Mass Spectrometric Techniques," *Anal. Biochem.*, Aug. 15, 2001; 295(2): 129-37.

Cai et al., "Capillary electrophoresis-mass spectrometry," *J. Chromatogr. A.*, Jun. 26, 1995; 703(1-2): 667-92.

Chapple et al., "Acquisition of Metabolic Profiling Instrumentation at Purdue," Grant Abstract, Grant No. DBI-0421102 [online]. National Science Foundation, project dates Sep. 1, 2004 to Aug. 31, 2008 [retrieved on Sep. 9, 2011]. Retrieved from the Internet: <URL:http://www.nsf.gov/awardsearch/showAward.do?AwardNumber=0421102>; 3 pgs.

Cohn, "The Separation of Purine and Pyrimidine Bases and of Nucleotides by Ion Exchange," *Science*, Apr. 15, 1949;109(2833): 377-8.

Coulier et al., "Simultaneous quantitative analysis of metabolites using ion-pair liquid chromatography-electrospray ionization mass spectrometry," *Anal. Chem.*, Sep. 15, 2006; 78(18): 6573-82.

de Koning et al., "A method for the determination of changes of glycolytic metabolites in yeast on a subsecond time scale using extraction at neutral pH," *Anal. Biochem.*, Jul. 1992; 204(1): 118-23.

Enrich et al., "Determination of adenine nucleotides in *Mytilus galloprovincialis* Lmk. by ion-pair high-performance liquid chromatography with a diode array detector," *J. Liq. Chromatogr. Relat. Technol.*, 1999; 22(9): 1391-402.

Entian et al., "A partial defect in carbon catabolite repression in mutants of *Saccharomyces cerevisiae* with reduced hexose phosphoryolation," *Mol. Gen. Genet.*, Nov. 4, 1977; 156(1): 99-105.

Feurle et al., "Analysis of phosphorylated carbohydrates by high-performance liquid chromatography-electrospray ionization tandem mass spectrometry utilising a β-cyclodextrin bonded stationary phase," *J Chromatogr. A.*, Apr. 17, 1998; 803(1-2): 111-9.

Fiehn et al., "Identification of Uncommon Plant Metabolites Based on Calculation of Elemental Compositions Using Gas Chromatography and Quadrupole Mass Spectrometry," *Anal. Chem.*, Aug. 1, 2000; 72(15): 3573-80.

Filatov et al., "Fluorescent immunoprecipitation analysis of cell surface proteins: A methodology compatible with mass-spectrometry," *J. Immunol. Methods*, Jan. 30, 2007; 319(1-2): 21-33. Available online Oct. 13, 2006.

Finney et al., "Systems biology markup language: Level 2 and beyond," *Biochem. Soc. Trans.*, Dec. 2003; 31(Pt. 6): 1472-3.

Ford et al., "Aqueous in situ derivatization of carboxylic acids by an ionic carbodiimide and 2,2,2-trifluoroethylamine for electron-capture detection," *J. Chromatogr. A.*, Mar. 23, 2007; 1145(1-2): 241-5. Available online Feb. 1, 2007.

Gancedo et al., "Concentrations of intermediary metabolites in yeast," *Biochimie*, 1973; 55(2): 205-11.

Gonzalez et al., "A rapid and reliable method for metabolite extraction in yeast using boiling buffered ethanol," *Yeast*, Nov. 1997; 13(14): 1347-55.

Groussac et al., "Improved protocols for quantitative determination of metabolites from biological samples using high performance ionic-exchange chromatography with conductimetric and pulsed amperometric detection," *Enzyme Microb. Technol.*, Jun. 1, 2000; 26(9-10): 715-23.

Hajjaj et al., "Sampling techniques and comparative extraction procedures for quantitative determination of intra- and extracellular metabolites in filamentous fungi," *FEMS Microbiol. Lett.*, Jul. 1, 1998; 164(1): 195-200.

Ho et al., "Genetically Engineered *Saccharomyces* Yeast Capable of Effective Cofermentation of Glucose and Xylose," *Appl. Environ. Microbiol.*, May 1998; 64(5): 1852-9.

Ho et al., "Successful Design and Development of Genetically Engineered *Saccharomyces* Yeasts for Effective Cofermentation of Glucose and Xylose from Cellulosic Biomass to Fuel Ethanol," *Adv. Biochem. Eng. Biotechnol.*, 1999; 65: 163-92.

Huck et al., "Profiling of Pentose Phosphate Pathway Intermediates in Blood Spots By Tandem Mass Spectrometry: Application to Transaldolase Deficiency," *Clin. Chem.*, Aug. 2003; 49(8): 1375-80.

Hull et al., "Separation and analysis of 4'-epimeric UDP-sugars, nucleotides, and sugar phosphates by anion-exchange high-performance liquid chromatography with conductimetric detection," *Anal. Biochem.*, Oct. 1994; 222(1): 49-54.

Hunt, "Substituent Effects (contd.)," Support materials designed for use with Carey, "Chapter 12: Reactions of Arenes. Electrophilic Aromatic Substitution," *Organic Chemistry*, McGraw-Hill, Columbus, Ohio, 2006 [online]. Retrieved from the internet Apr. 29, 2008. Available online. <URL: http://www.chem.ucalgary.ca/courses/351/Carey5th/Ch12/ch12-8d.html>, 3 pgs.

Ivanovskaya et al., "Modification of Oligo (Poly) Nucleotide Phosphomonoester Groups in Aqueous Solutions," *Nucleosides & Nucleotides*, 1987; 6(5): 913-34. Available online Dec. 13, 2006.

Jensen et al., "Determination of the phosphorylated sugars of the Embden-Meyerhoff-Parnas pathway in *Lactococcus lactis* using a fast sampling technique and solid phase extraction," *Biotechnol. Bioeng.*, May 5, 1999; 63(3): 356-62.

Kubota et al., "Development of an HPLC-flourescence determination method for carboxylic acids related to the tricarboxylic acid cycle as a metabolome tool," *Biomed. Chromatogr.*, Dec. 2005; 19(10): 788:95.

Lange et al., "Improved rapid sampling for in vivo kinetics of intracellular metabolites in *Saccharomyces cerevisiae*," *Biotechnol. Bioeng.*, Nov. 20, 2001; 75(4): 406-15.

Lu et al., "A high-performance liquid chromatography-tandem mass spectrometry method for quantitation of nitrogen-containing intracellular metabolites," *J. Am. Soc. Mass. Spectrom.*, Jan. 2006; 17(1): 37-50. Available online Dec. 15, 2005.

Luo et al., "Simultaneous determination of multiple intracellular metabolites in gycolysis, pentose phosphate pathway and tricarboxylic acid cycle by liquid chromatography-mass spectrometry," *J. Chromatogr. A.*, Apr. 20, 2007; 1147(2): 1543-64. Available online Feb. 16, 2007.

Ma et al., "Recent advances in applications of liquid chromatography-tandem mass spectrometry to the analysis of reactive drug metabolites," *Chem. Biol. Interact.*, Apr. 15, 2009; 179(1): 25-37. Available online Sep. 19, 2008.

Mashego et al., "Microbial metabolomics: past, present and future methodologies," *Biotechnol. Lett.*, Jan. 2007; 29(1): 1-16. Available online Nov. 8, 2006.

Masson et al., "Simple cation-exchange high-performance liquid chromatography optimized to the measurement of metabolites in the effluents from perfused rat livers using refractive index and ultraviolet detectors," *J. Chromatogr.*, Feb. 15, 1991; 563(2): 231-42.

(56) References Cited

OTHER PUBLICATIONS

Nielsen, "Metabolic engineering: techniques for analysis of targets for genetic manipulations," *Biotechnol. Bioeng.*, Apr. 20-May 5, 1998; 58(2-3): 125-32.

Picioreanu et al., "Potentiometric detection of carboxylic acids, phosphate esters, and nucleotides in liquid chromatography using anion-selective coated-wire electrodes," *Anal. Chem.*, May 1, 2000; 72(9): 2029-34.

Qian et al., "Determination of adenosine nucleotides in cultured cells by ion-pairing liquid chromatography-electrospray ionization mass spectrometry," *Anal. Biochem.*, Feb. 1, 2004; 325(1): 77-84.

Regnier et al., "Tools for Differential Metabolomics," Grant Abstract, Grant No. R33DK070290 [online]. National Institute of Diabetes and Digestive and Kidney Diseases; National Institutes of Health, project dates Sep. 30, 2004 to Jul. 31, 2008 [retrieved on Jan. 28, 2013]. Retrieved from the Internet: <http://projectreporter.nih.gov/pr_Prj_info_desc_dtls.cfm?aid=7105088&icde=15104654&ddparam=&ddvalue=&ddsub=&cr=1&csb=default&cs=ASC&print=yes>; 2 pgs.

Ritter et al., "High-performance anion-exchange chromatography using on-line electrolytic eluent generation for the determination of more than 25 intermediates from energy metabolism of mammalian cells in culture," *J. Chromatogr. B. Analyt. Technol. Biomed. Life Sci.*, Nov. 7, 2006; 843(2): 216-26. Available online Jun. 23, 2006.

Roessner et al., "Metabolic Profiling Allows Comprehensive Phenotyping of Genetically or Environmentally Modified Plant Systems," *Plant Cell*, Jan. 2001; 13(1): 11-29.

Ruijter et al., "Determination of intermediary metabolites in *Aspergillus niger*," *J. Microbiol. Methods*, Jun. 1996; 25(3): 295-302.

Ruijter et al., "Characterisation of the *Aspergillus nidulans* frA1 mutant: hexose phosphorylation and apparent lack of involvement of hexokinase in glucose repression," *FEMS Microbiol. Lett.*, Jun. 1, 1996; 139(2-3): 223-8.

Sedlak et al., "In vitro $^{13}C$ labeling for simultaneous identification and quantification of central carbon intermediates in genetically modified *Saccharomyces* yeast capable of glucose/xylose co-fermentation using reverse phase liquid chromatography-mass spectrometry," Abstract and Poster No. 2-38. *30$^{th}$ Symposium on Biotechnology for Fuels and Chemicals*, New Orleans, LA: May 4, 2008. Abstract also available online [retrived on Sep. 1, 2011]. Retrieved from the Internet: <http://sim.confex.com/sim/30th/techprogram/P5870.HTM>. 3 pages total.

Sekiguchi et al., "Development of a comprehensive analytical method for phosphate metabolites in plants by ion chromatography coupled with tandem mass spectrometry," *J. Chromatogr. A.*, Aug. 26, 2005; 1085(1): 131-6.

Smits et al., "Cleanup and analysis of sugar phosphates in biological extracts by using solid-phase extraction and anion-exchange chromatography with pulsed amperometric detection," *Anal. Biochem.*, Jul. 15, 1998; 261(1): 36-42.

Soga et al., "Simultaneous determination of anionic intermediates for *Bacillus subtilis* metabolic pathways by capillary electrophoresis electrospray ionization mass spectrometry," *Anal. Chem.*, May 15, 2002; 74(10): 2233-9.

Stephanopoulos et al., "Exploiting biological complexity for strain improvement through systems biology," *Nat. Biotechnol.*, Oct. 2004; 22(10): 1261-7.

Tao, "Soluble polymer-based isotopic labeling (SoPIL): a new strategy to discover protein biomarkers?" *Expert Rev. Proteomics*, Oct. 2007; 4(5): 603-7.

Tatár et al., "Determination of Organic Acids in Xylem Sap of Cucumber: Effect of Lead Contamination," *Microchem. J.*, Mar. 1998; 58(3): 306-14.

Theobald et al., "In vivo analysis of metabolic dynamics in *Saccharomyces cerevisiae*: I. Experimental observations," *Biotechnol. Bioeng.*, Jul. 20, 1997; 55(2): 305-16.

Toya et al., "Direct measurement of isotopomer of intracellular metabolites using capillary electrophoresis time-of-flight mass spectrometry for efficient metabolic flux analysis," *J. Chromatogr. A.*, Aug. 3, 2007; 1159(1-2): 134-41. Available online Apr. 13, 2007.

Tuytten et al., "Short capillary ion-pair high-performance liquid chromatography coupled to electrospray (tandem) mass spectrometry for the simultaneous analysis of nucleoside mono-, di- and triphosphates," *Rapid Commun. Mass Spectrom.*, 2002; 16(12): 1205-15.

van Dam et al., "Analysis of glycolytic intermediates in *Saccharomyces cerevisiae* using anion exchange chromatography and electrospray ionization with tandem mass spectrometric detection," *Anal. Chim. Acta*, Jun. 5, 2002; 460(2): 209-18. Available online Apr. 19, 2002.

Vogt et al., "Simultaneous detection of high energy phosphates and metabolites of glycolysis and the Krebs cycle by HPLC," *Biochem. Biophys. Res. Commun.*, Jul. 30, 1998; 248(3): 527-32.

Wamelink et al., "Quantification of sugar phosphate intermediates of the pentose phosphate pathway by LC-MS/MS: application to two new inherited defects of metabolism," *J. Chromatogr. B. Analyt. Technol. Biomed. Life Sci.*, Aug. 25, 2005; 823(1): 18-25. Available online Jan. 23, 2005.

Wittmann et al., "Dynamics of intracellular metabolites of glycolysis and TCA cycle during cell-cycle-related oscillation in *Saccharomyces cerevisiae*," *Biotechnol. Bioeng.*, Mar. 30, 2005; 89(7): 839-47.

Womersley et al., "Separation of tricarboxylic acid cycle acids and other related organic acids in insect haemolymph by high-performance liquid chromatography," *J. Chromatogr. A.*, 1985; 318: 112-6.

Yang et al., "Enhancement of Amino Acid Detection and Quantification by Electrospray Ionization Mass Spectrometry," *Anal. Chem.*, Jul. 1, 2006; 78(13): 4702-8. Available online May 17, 2006.

Yang et al., "Enhancement of the LC/MS Analysis of Fatty Acids through Derivatization and Stable Isotope Coding," *Anal. Chem.*, Jul. 15, 2007; 79(14): 5150-7. Available online May 11, 2007.

Yang et al., "Stable isotope-coded quaternization for comparative quantification of estrogen metabolites by high-performance liquid chromatography-electrospray ionization mass spectrometry," *J. Chromatogr. B.*, Jul. 15, 2008; 870(2): 233-40.

Yang et al., "Comparative metabolite profiling of carboxylic acids in rate urine by CE-ESI MS/MS through positively pre-charged and $^{2}H$-coded derivatization," *Electrophoresis*, Nov. 2008; 29(22): 4549-60. Available online Nov. 26, 2008.

Yang et al., "Simultaneous Quantification of Metabolites Involved in Central Carbon and Energy Metabolism Using Reversed-Phase Liquid Chromatography Mass Spectrometry and in Vitro $^{13}C$ Labeling," *Anal. Chem.*, 2008; 80(24): 9508-16. Available online Nov. 14, 2008.

Zielinska et al., "Potentiometric detection of organic acids in liquid chromatography using polymeric liquid membrane electrodes incorporating macrocyclic hexaamines," *J. Chromatogr. A.*, Apr. 27, 2001; 915(1-2): 25-33.

International Preliminary Report on Patentability, issued Nov. 2, 2010, by the PCT, in Patent Application No. PCT/US2009/002711, filed May 1, 2009; 5 pgs.

International Search Report, issued Dec. 16, 2009, by the PCT, in Patent Application No. PCT/US2009/002711, filed May 1, 2009; 3 pgs.

Written Opinion of the International Searching Authority, issued Dec. 16, 2009, by the PCT, in Patent Application No. PCT/US2009/002711, filed May 1, 2009; 4 pgs.

\* cited by examiner

GROUP SPECIFIC INTERNAL STANDARD TECHNOLOGY (GSIST) FOR SIMULTANEOUS IDENTIFICATION AND QUANTIFICATION OF SMALL MOLECULES

CONTINUING APPLICATION DATA

This application is the §371 U.S. National Stage of International Application No. PCT/US2009/002711, filed 1 May 2009, which claims the benefit of U.S. Provisional Application Ser. No. 61/126,235 filed May 2, 2008, each of which are incorporated by reference herein.

GOVERNMENT FUNDING

This invention was made with government support under Grant No. R33DK070290, awarded by the National Institutes of Health, Grant No. DE-FC36-07GO17059, awarded by the U.S. Department of Energy, and Grant No. DBI0421102, awarded by the National Science Foundation. The Government has certain rights in the invention.

BACKGROUND

Although life is based on a fixed genetic blueprint, living systems are dynamic, each developing, surviving, and proliferating in a different way. In responding to change, organisms must themselves change. Signaling, gene activation or suppression, transcription, translation, post-translational modifications, intracellular transport, metabolic processing, and feedback control at the gene, protein, and metabolite level all involve material changes in cells. This almost always occurs through a change in the concentration or flux of cellular components as opposed to changes in their structure. Finding and quantifying these patterns of change is a critical issue in studying regulation and understanding the change that defines biological systems.

Metabolomics is the identification and quantification of all the small molecules present inside or excreted by cells. Although knowledge of the small molecules in cells is a necessary first step in understanding metabolism (Fiehn et al., 2000 *Analytical Chemistry* 72(15): 3573-80; Roessner et al., 2001 *Plant Cell* 13(1): 11-29) monitoring changes in their concentration and flux provide deeper insight into cellular physiology.

Major technological advances of the post-genomic era now permit rapid mRNA, protein and ion profiling that are useful in analyzing the proteome and transcriptome. However, the metabolome is unique from the proteome and transcriptome in that it is not directly encoded by the genome. Nonetheless, the ability to quantify and characterize the metabolome is critical for understanding not only role of metabolites in living system but also to elucidate protein function. Transformation of substrate to product is affected either directly though the functional changes of protein or indirectly through protein ability to interact with the other proteins. Likewise, different levels of metabolites can affect the function of other proteins directly by interaction with them or indirectly through changes in physical-chemical conditions inside the cell (low levels of ATP, change in pH etc.). Furthermore, low molecular weight molecules are important components in the communication network among cells, tissues and even whole organisms (e.g. pheromones). Quantification of metabolites is of major importance in elucidating the regulatory impact of metabolites in biological systems (Fiehn et al., *Analytical Chemistry* 2000, 72:3573-3580). Thus precise quantification of change metabolite concentrations is key element system biology and hold significant promise to identify important relationships between these molecules, proteins and other gene products.

Among the whole cellular metabolic network, central carbon metabolism, which is composed of glycolysis, the pentose-phosphate pathway, and the tricarboxylic acid cycle (TCA), plays a key function in the substrate degradation, energy and cofactor regeneration, and biosynthetic precursor supply. The structure of the metabolic reaction network has been mapped in substantial detail, but comprehensive quantitative analysis of the rates and regulation of cellular metabolic reactions remains a major interest for various biofields, such as enzyme kinetics and enzyme expression patterns (Gancedo and Gancedo, 1973 *Biochimie* 55(2): 205-11; Entian et al., 1977 *Molecular & General Genetics* 156(1): 99-105), metabolic engineering (Nielsen, 1998 *Biotechnology & Bioengineering* 58(2-3): 125-32) and microbial metabolomics (Mashego et al., 2007 *Biotechnology Letters* 29(1): 1-16). Methodology development to efficiently and accurately measure intracellular intermediate metabolite concentrations under in vivo conditions remains a significant challenge in the study of central carbon metabolism.

There are more than 35 intermediates directly involved in central carbon metabolism, which belong to four categories of chemical compounds: phosphorylated sugars, phosphocarboxylic acids, carboxylic acids, and nucleotides and cofactors. Precise quantification of these intercellular intermediates under in vivo conditions comes with a unique set of challenges from sampling, metabolite extraction, and analytical methods. The intracellular turnover rates for many metabolites are in the range of seconds (De Koning and van Dam, 1992 *Anal. Biochem.* 204: 118-123), thus, to gain an accurate picture of metabolic concentrations requires a fast sampling and instant deactivation of the enzymatic activity with preservation of cell integrity. Moreover, complete extraction of the metabolites is also essential to reflect in vivo metabolic concentrations. Well-documented methods of sampling, quenching and extraction for yeast are available that comply with these criteria (Gonzalez et al., 1997 *Yeast* 13(14): 1347-55; Lange et al., 2001 *Biotechnology & Bioengineering* 75(4): 406-15). The analytical tools for these metabolites have actually existed for several decades; however, analytical methodology has fallen behind the increasing demand from systems biology. Major challenges in the method development arise from the low abundance of most intracellular metabolites, difficulties in distinguishing between metabolites in the same category due to their similarities, and the challenge in developing an effective measurement method due to the diversity between different groups in chemical structure and properties. There appears to be no such available method that could reliably and simultaneously quantify all the intermediates from central carbon metabolism.

Although enzyme-based assays for individually determining certain metabolites have been available for some time (Hajjaj et al., *FEMS Microbiol. Lett.* 1998, 164:195-200; Ruijter and Visser, *J. Microbiol. Methods* 1996, 25:295-302; Theobald et al., *Biotechnol. Bioeng.* 1997, 55:305-316), these assays are time-consuming, and limited to small number of metabolites, depending on the availability of the enzymes. Capillary electrophoresis-mass spectrometry (CE-MS) is a promising tool for ionic metabolites analysis (Soga et al., *Anal Chem* 2002, 74:2233-2239; Toya et al., *J Chromatogr A* 2007, 1159:134-141), but generally robustness and sensitivity need to be improved (Cai and Henion, *J Chromatogr A* 1995, 703:667-692). Currently, liquid chromatography (LC) is a predominant technique for these studies. Due to the anionic property of most metabolites, anion-exchange chromatography (AEC) with UV detection is a commonly used detection method. AEC was first used for the analysis of nucleotides (Cohn, *Science* 1949, 109:377-378). When the use of AEC was extended to sugar phosphates or carboxylic acids, other detection techniques, such as pulsed amperometric detection (Groussac et al., *Enzyme Microb Technol* 2000, 26:715-723; Jensen et al., *Biotechnol Bioeng* 1999, 63:356-362; Smits et al., *Anal Biochem* 1998, 261:36-42), potentiometric detection (Picioreanu et al., *J. Anal Chem* 2000, 72:2029-2034) or conductimetric detection (Groussac et al., *Enzyme Microb Technol* 2000, 26:715-723; Bhattacharya et al., *Anal Biochem* 1995, 232:98-106; Hull and Montgomery, *Anal Biochem* 1994, 222:49-54; Ritter et al., *J Chromatogr B Analyt Technol Biomed Life Sci* 2006, 843:216-226; Vogt et al., *Biochem Biophys Res Commun* 1998, 248:527-532) were used to circumvent metabolites insufficient UV absorbance, and consequently low UV detection sensitivity.

One of the most common ways of analyzing metabolites is through separation by gas chromatography (GC) or liquid chromatography (LC) followed by identification and quantification through mass spectrometry (MS) (Stephanopoulos et al., *Nature Biotechnology* 2004, 22:1261-1267; Wamelink et al., *J Chromatogr B Analyt Technol Biomed Life Sci* 2005: 823, 18-25). In the case of a complicated pool of metabolites, one-dimensional LC separation is not sufficient to resolve the multiple metabolites involved. As a powerful detection and quantification tool, mass spectrometry (MS) is also capable of offering a second chance for increased resolution by discriminating molecules based on their m/z values. In addition, tandem MS provides fragmentation information for metabolites structure elucidation and for quantification by selected reaction monitoring (SRM). MS has been widely applied into various LC separation modes for this application. In AEC-MS, due to the high concentration of non-volatile salts in the eluent, which is not acceptable for MS, it was a common practice to mount an after-column desalting device before the eluent enters the MS (van Dam et al., 2002 *Anal. Chem. Acta* 460: 209-218; Sekiguchi et al., 2005 *J Chromatogr A* 1085 (1): 131-6; Wittmann et al., 2005 *Biotechnol Bioeng* 89(7): 839-47), which might reduce the separation efficiency. Alternatively, hydrophilic interaction chromatography (HILIC)-tandem MS has been reported to measure large number of cellular metabolites although the analyses were not performed simultaneously (Bajad et al., 2006 *J Chromatogr A* 1125(1): 76-88).

Among all LC separation modes, reverse phase chromatography (RPLC) is still preferred because of its high separation efficiency, versatility and compatibility with MS. However, in the instance of central carbon intermediates, standard RPLC is ineffectual because these very polar metabolites nearly have no retention on the stationary phases. Although beta-cyclodextrin columns in reverse phase mode (and normal phase mode) have been used for the separation of sugar phosphates, most of the analytes eluted at nearly the dead volume (Feurlea et al., 1998 *J Chromatogr A* 803: 111-19; Buchholz et al., 2001 *Anal Biochem* 295(2): 129-37). This situation can be significantly changed by adding ion pairing reagents to the mobile phase, i.e. ion pairing RPLC. This type of reagent should be volatile in compliance with MS detection, such as dimethylhexylamine for nucleotides separation (Tuytten et al., 2002 *Rapid Commun Mass Spectrom* 16(12): 1205-15; Qian et al., 2004 *Anal Biochem* 325(1): 77-84), hexylamine for nucleotides, coenzyme A esters, sugar nucleotides, and sugar bisphosphates (Coulier et al., 2006 *Anal Chem* 78: 6573-82), and octylamine for the separation of pentose phosphate pathway intermediates in blood spots (Finney and Hucka, 2003 *Biochem Soc Trans* 31(Pt 6): 1472-3; Wamelink et al., 2005 *J Chromatogr B Analyt Technol Biomed Life Sci* 823(1): 18-25). Oldiges published an ion pairing RPLC-tandem MS method recently, using tributylammonium acetate as an ion paring reagent (Filatov et al., 2007 *J Immunological Methods* 319(1-2): 21-33). Twenty-three metabolites from central carbon metabolism in the *E. coli* cell extract were simultaneously detected.

Signal intensity of an analyte in MS depends on its concentration and ionization efficiency. Due to ion suppression these methods have significant problems with precision of quantification. Additionally, ionization efficiency not only varies between analytes but can depend on other components in the matrix, particularly in the case of electrospray ionization (ESI) as used in LC-MS. This problem can theoretically be addressed in LC-MS quantification through the use of a $^{13}C$-coded internal standard that co-elutes with the analyte and has an ionization environment identical to the analyte. Synthesizing the requisite $^{13}C$-coded internal standard is generally simple when the number of analytes being determined is small. However, when large, the requisite number of syntheses can become prohibitive. Although it is possible to biosynthesize $^{13}C$-coded metabolites as was done for D-$^{13}C_6$-glucose 6-phosphate (Huck et al., *Clin Chem* 2003, 49:1375-1380), and although some $^{13}C$-coded metabolites are commercially available, a comprehensive collection of internal standard metabolites is generally not available. Some have used standard addition methods for MS quantification (Huck et al., *Clin Chem* 2003, 49:1375-1380; Buchholz et al., *Anal Biochem* 2001, 295:129-137; Luo et al., *J Chromatogr A* 2007, 1147:153-164; van Dam et al., *Anal. Chem. Acta* 2002, 460:209-218) to circumvent this problem. However, the MS response can change over time due to changes in the MS instrument (Coulier et al., *Anal Chem* 2006, 78:6573-6582).

Regnier et al. (U.S. Pat. No. 6,864,099, issued Mar. 8, 2005, and U.S. Pat. No. 6,872,575, issued Mar. 29, 2005) describe a method for mass spectrometric analysis of peptide or protein analytes in a biological sample. The method, referred to as the global internal standard technology (GIST) method, involves differential isotopic labeling of analytes in control and experimental samples such that analytes in the control samples function as internal standards. Metabolites, such as proteins (or peptides if proteolysis is employed) in control and experimental samples are post-synthetically derivatized with chemically equivalent but isotopically distinct forms of a labeling agent, mixed, then subjected to mass spectrometric analysis to determine relative concentrations. The labeling agent is selected so as to react with a particular functional group, such as an amine group or a carboxylic acid, present on the protein or peptide of interest. Labeling reagents useful for labeling amino acids (Yang et al., 2006, *Anal. Chem.*, 78:4702; Regnier et al., PCT Publication WO2007/117665, published Oct. 18, 2007), carboxylic acids (Yang et al., *Electrophoresis* 2008, 29:4549-4560), estrogen metabolites (Yang et al., 2008 *J. Chromatog. B*, 870:233-240) and fatty acids (Yang et al., 2007, *Anal Chem* 79:5150-5157) have also been described. Metabolites, as a general class of compounds, however, have no single, common functional group that can be used for isotope coding. Thus, a number of reagents would be needed in order to achieve truly global internal standard quantification (Yang et al., 2007, *Anal Chem* 79:5150-5157). Simultaneous analysis of multiple analytes in two or more samples and relative quantification of metabolites by ESI-MS using labeling reagents that are reactive to particular compound classes has been reported by Shortreed et al. (PCT Publication WO2007/109292, published Sep. 27, 2007).

SUMMARY OF THE INVENTION

The present invention provides reagents and methods that permit simultaneous analysis of multiple diverse small molecule analytes, such as metabolites, present in a complex mixture, thereby facilitating rapid detection, identification and/or quantification of multiple components of a metabolic pathway, including both primary and secondary metabolites. A single reagent simultaneously derivatizes small molecule analytes having different reactive functional groups. Metabolites and other small molecule analytes derivatized in accordance with the method of the invention may contain, without limitation, one or more functional groups, for example one or more carbonyl, phosphate and/or carboxyl groups. Experimental and control (or reference) samples that contain a multiplicity of small molecule analytes having different reactive functional groups are labeled with chemically identical but isotopically distinct forms of the labeling reagent. The isotope label present in the labeling reagent is a mass isotope and is preferably a mass isotope of carbon, such as $^{13}C$, but can also be a mass isotope of nitrogen, sulfur, oxygen or hydrogen, such as $^{15}N$, $^{34}S$, $^{18}O$ or $^{2}H$, respectively. The labeled samples are analyzed using mass spectrometry.

In one embodiment, the invention provides a method for identifying and/or quantifying a plurality of small molecule analytes present in a sample. A control sample that includes known quantities of the small molecule analytes is obtained or prepared. The control sample contains multiple analytes that contain different types of reactive functional groups. To the control sample is added a first isotopic variant of a labeling reagent, such that the labeling reagent contacts each analyte to yield a plurality of first isotopically labeled analytes. The labeling reagent is covalently linked to the analytes at the different reactive functional groups. An experimental sample is also provided, which likewise contains a plurality of the small molecule analytes. A second isotopic variant of the labeling reagent is added to the experimental sample, such that the labeling reagent contacts each analyte to yield a plurality of second isotopically labeled analytes. The first and second isotopically labeled analytes are chemically equivalent yet isotopically distinct. Portions of the control and experimental samples are mixed to yield a combined sample; and the combined sample is subjected to mass spectrometric analysis to identify and/or quantify the plurality of analytes in the experimental sample. Since this method involves the use of known small molecule standards, absolute quantification can be achieved.

To achieve greater precision in the quantification of the small molecule analytes, the present invention provides a variation of the method that incorporates the concept of standard addition. In this embodiment of the method, control and experimental samples are provided as described, but prior to labeling the experimental sample into first and second experimental subsamples. An amount of the control sample is added to the first experimental subsample. The first isotopic variant of a labeling reagent is then added to the control sample so as to contact each said analyte in the control sample to yield a plurality of first isotopically labeled analytes, wherein the labeling reagent is covalently linked to the analytes at the different reactive functional groups. The second isotopic variant of the labeling reagent is added to both the first and second experimental subsamples so as to contact each said analyte in the subsamples to yield first and second experimental subsamples each comprising a plurality of second isotopically labeled analytes, wherein the first and second isotopically labeled analytes are chemically equivalent yet isotopically distinct. Equal amounts of the control sample are then added to each of the first and second experimental subsamples to yield first and second combined samples, and the first and second combined samples are subjected to mass spectrometric analysis. Peak intensities generated by the first and second combined samples are compared to quantify the plurality of analytes in the experimental sample.

In another embodiment, the invention provides a method for relative quantification of small molecule analytes in a sample. This method permits detection of differences in the concentrations of a plurality of small molecule analytes present in an experimental sample, and a reference or control sample (i.e., first and second samples, respectively). First and second samples are provided, each sample comprising a plurality of small molecule analytes, each analyte comprising a different reactive functional group. A first isotopic variant of a labeling reagent is contacted with each said analyte in the first sample to yield a plurality of first isotopically labeled analytes, wherein the labeling reagent is covalently linked to the analytes at the different reactive functional groups; and a second isotopic variant of the labeling reagent is contacted with each said analyte in the second sample to yield a plurality of second isotopically labeled analytes, wherein the first and second isotopically labeled analytes are chemically equivalent yet isotopically distinct. Portions of the first and second samples are mixed to yield a combined sample. The combined sample is subjected to mass spectrometric analysis to determine a normalized isotope ratio characterizing analytes whose concentration is the same in the first and second samples and an isotope ratio of the first and second isotopically labeled analytes, wherein a difference in the isotope ratio of the first and second isotopically labeled analytes and the normalized isotope ratio is indicative of a difference in concentration of the analyte in the first and second samples.

In another embodiment, the invention provides a method for identifying a small molecule analyte in a sample. This embodiment of the method typically does not involve the use of a separate (different) control or reference sample. A sample containing a plurality of small molecule analytes, each analyte comprising a different reactive functional group, is divided into at least first and second portions. A first isotopic variant of a labeling reagent is contacted with each said analyte in the first portion to yield a plurality of first isotopically labeled analytes, wherein the labeling reagent is covalently linked to the analytes at the different reactive functional groups. A second isotopic variant of the labeling reagent is contacted with each analyte in the second portion to yield a plurality of second isotopically labeled analytes, wherein the first and second isotopically labeled analytes are chemically equivalent yet isotopically distinct. The first and second portions are combined, and the combined sample is subjected to mass spectrometric analysis to yield m/z values for at least one analyte. The m/z values are then compared to known or predicted m/z values for a known analyte in order to identify the analyte.

The labeling reagent used in the method of the invention is preferably an amine and preferably includes a hydrophobic moiety, such as an aryl group. A particularly preferred labeling reagent is aniline, including a substituted aniline or an aniline derivative. The heavy mass isotope variant of the labeling reagent preferably includes $^{13}C$. A particularly preferred labeling reagent includes at least three $^{13}C$ atoms. The labeling reaction preferably occurs in the presence of ethylcarbodiimide hydrochloride (EDC). Optionally, prior to mass spectrometric analysis, samples can be fractionated. Fractionation, if performed, is preferably accomplished using reverse phase liquid chromatography (RPLC).

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

DETAILED DESCRIPTION OF ILLUSTRATIVE EMBODIMENTS

Figure 1:
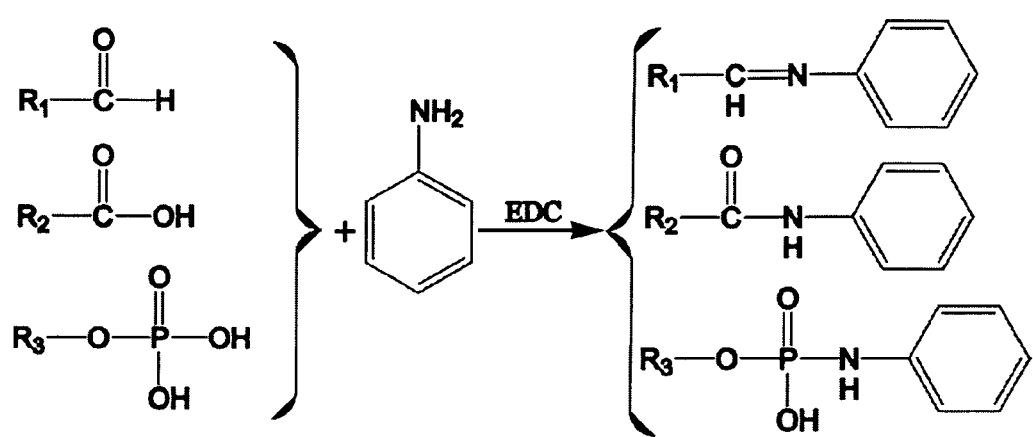
FIG. 1 shows the general labeling schemes for carbonyl, phosphoryl and carboxyl with aniline.

The invention is directed to a post-biosynthetic in vitro method for simultaneously analyzing a multiplicity of small molecule analytes in a complex sample. The method is particularly well-suited for identifying and quantifying a plurality of metabolites in a biological sample. The method permits concurrent identification, detection and/or quantification of multiple components of a metabolic pathway, and in that respect can be considered a "pathway targeted approach." The method of the invention is referred to herein as "Group Specific Internal Standard Technology" (GSIST).

In GSIST, chemically identical but isotopically distinct labeling reagents are used to label experimental and control samples that contain a multiplicity of small molecule analytes having different reactive functional groups. The control sample can be, for example, a mixture of known standards, or it can be a biological sample. The derivatization agent is a multifunctional reagent that is capable of reacting with more than one functional group, thereby expanding the set of metabolites that is derivatized during a single derivatization reaction. After derivatization, the samples are mixed together. Mass spectrometric analysis of the labeled small molecule analytes can be used to identify the small molecule analytes as well as to effect relative or absolute quantification. Each derivatized metabolite from the control sample serves as an internal standard for determining the relative or absolute concentration of the corresponding chemically identical but isotopically distinct derivatized component in experimental sample. In this context, chemical equivalence is defined by identical chromatographic and electrophoretic behavior, such that the two metabolites cannot be separated from each other using standard laboratory purification and separation techniques. For example, a metabolite present in each sample may, after labeling, differ in mass by a few atomic mass units when the metabolite from one sample is compared to the metabolite from the other sample (i.e., they are isotopically distinct). However, these two metabolites would ideally be chemically equivalent as evidenced by their identical chromatographic behavior and electrophoretic migration patterns.

Optionally, either before or after labeling, the samples can be subjected to separation or analysis in a second dimension, such as a chromatography step, preferably reverse phase liquid chromatography (RPLC), or an electrophoresis step, such as gel electrophoresis.

The invention further provides a new quantification method for mass spectrometry, referred to herein as Global Isotope-Labeled Internal Standard Addition (GILISA). GILISA can be used as a quantification method in conjunction with the labeling method of GSIST. GISILA takes into account both instrument variation as well as variation in derivatization efficiency, due for example to different sample matrix environments. In GILISA, as described in more detail below, an isotopically labeled metabolite standard, such as a metabolite standard labeled with $^{13}C_6$-aniline, serves as an internal standard for precise MS quantification of a corresponding metabolite in an experimental sample.

Labeling Agent

Derivatization agents directed to one functional group, such as those that target primary amines or carboxy groups, work well for classes of compounds such as proteins and peptides, but they have drawbacks when the object is to analyze metabolic pathways because not all molecules in a pathway contain the same functional group. To solve this problem the present invention provides a multifunctional reagent, exemplified by an aniline based derivatization agent, that derivatizes more than one functional group and is therefore more suitable for metabolic pathways analyses.

Many metabolites and other small molecule analytes can be classified acids, aldehydes, or phosphates. They often contain a carbonyl (e.g., an aldehyde or ketone group), a phosphate and/or a carboxyl group and are particularly amenable to labeling according to the present method. Typical derivatization agents target only one specific functional group (e.g., carbonyl, phosphate or carboxyl), but the labeling agent of the present invention targets two or more specific functional groups, resulting in a more global approach to labeling metabolites and other small molecule analytes.

The multifunctional labeling reagent provided by the present invention is capable of labeling a variety of small molecule analytes containing different reactive functional groups. The reagent is selected so as to label as many small molecules as possible or desirable. In an exemplary embodiment, the multifunctional labeling agent introduces $^{13}$C-coded hydrophobic moieties into the most of the small molecules in a biological sample. Preferably the labeling reagent can react with at least two different functional groups; more preferably, at least three different functional groups; and most preferably, at least three or more different functional groups. Optimized reaction conditions are provided that allow the labeling reagent to simultaneously react with the multiplicity of small molecule analytes containing the various reactive functional groups in a single step.

The multifunctional labeling agent contains a reactive functional group, preferably an electron donor group, more preferably a nucleophilic electron donor group. Preferred electron donor groups include a hydroxyl or an amine, more preferably a primary amine that reacts with at least one functional group present on a small molecule analyte. Aliphatic or aromatic amines may be used as labeling agents, although aromatic amines are preferred. Preferably, the amine is directly linked to the aromatic or heterocyclic ring, since this structure yields a stable product due to resonance structure. The ring is optionally substituted. Substituent(s), if present, can be positioned at the ortho (o-), meta (m-) or para (p-) position relative to the amine.

The method of the invention utilizes a pair of chemically identical but isotopically distinct labeling agents, referred to herein as isotopic variants. The isotope label is a heavy mass isotope label and is preferably a mass isotope of carbon, such as $^{13}$C, but can also be a mass isotope of nitrogen, sulfur, oxygen or hydrogen, such as $^{15}$N, $^{34}$S, $^{18}$O or $^{2}$H, respectively. The heavy isotopic variant of the labeling agent may contain one or two heavy mass isotope atoms, such as $^{13}$C atoms, but preferably contains at least 3, 4, 5 or 6 heavy mass isotope atoms.

Preferably the labeling reagent also includes a hydrophobic moiety, such as an alkyl or aryl group. More preferably, the labeling agent includes an aromatic or heterocyclic ring. The heteroatom, if present, can be O, S, or N, but is preferably nitrogen (N); preferably the heteroatom is located meta or para to the amine. The hydrophobic moiety facilitates retention and separation of the small molecule analytes in the sample when the sample is subjected to hydrophobic chromatography, such as reverse phase liquid chromatography (RPLC) prior to mass spectrometric analysis. Furthermore, an enhancement in peak intensity results from the increase in analyte hydrophobicity after labeling.

Thus, a preferred labeling reagent is an aromatic or heterocyclic amine, optionally substituted with one or more substituents present at the o-, m- or p-positions. In a particularly preferred embodiment, the labeling agent is a substituted or unsubstituted aromatic or heterocyclic primary amine, such as an aniline or a pyridine amine. If substituted, the ring can contain 1, 2, 3, 4 or 5 substituents. An exemplary labeling agent is an aniline, including a substituted aniline and an aniline derivative. $^{13}$C$_6$-aniline is readily available from, for example, Sigma-Aldrich. Ring substituents, if present, are preferably electron-donating groups, more preferably electron-donating groups independently selected from groups such as an alkyl, —R; ether, —O—R; ester, —O—(C=O)—R or —(C=O)—O—R; amide, —(C=O)—N—R or —N—(C=O)—R; or a secondary amine, —NHR; where R is an alkyl (linear or branched, saturated or unsaturated) or an aryl group. The number of carbon atoms in an R group present in a ring substituent can be 1, 2, 3, 4, 5, 6, 7, 8, 9, 10, 11, 12, 13, 14, 15, 16, 17, 18, 19, or 20 or more. Preferably, a ring substituent contains an R group having between 1 and 6 carbons (i.e., $C_1$-$C_6$), more preferably between 1 and 3 carbons (i.e., $C_1$-$C_3$). Optionally, a ring substituent may contain other groups such as a halide.

An example of a preferred labeling reagent is:

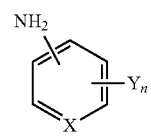
(I)

X=C(H) or N;
Y is independently selected from:

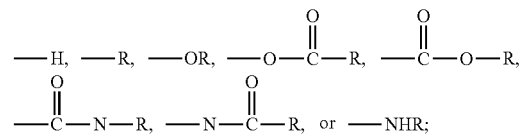

and
n=0, 1, 2, 3, 4 or 5
where R is independently an alkyl (linear or branched, saturated or unsaturated) or an aryl group.

Small molecule analyte functional groups that may react with the labeling agent include, but are not limited to, carbonyl, carboxyl, carbonate, aldehyde, ketone, phosphonyl, phosphate, phosphone, lactone, lactam and the like. Additional examples of functional groups present in a small molecule analyte such as a metabolite that may react with the labeling reagent include those that contain —C=X; —S=X; or —P=X; where X is O, N or S.

In a preferred embodiment, the labeling reagent simultaneously labels small molecule analytes containing carbonyl, a carboxylic acid, and/or a phosphate group; particularly preferred is a labeling reagent that simultaneously reacts with a carbonyl, a carboxylic acid, and a phosphate group.

The multifunctional labeling agent is capable of labeling many different biological metabolites, including both primary metabolites, such as those associated with a metabolic pathway such as the carbon cycle, and secondary metabolites, such as those not directly involved in the growth, development or reproduction of an organism. The method of the invention can be therefore used to analyze any small, organic molecules, such as metabolites, intermediates, substrates, and the like, that are involved in biological or cellular processes. Small molecule metabolites that include functional groups capable of reacting with the labeling reagent provided by the invention may include sugars, including aldoses and ketoses, nucleotides, nucleosides, lipids, and generally any organic intermediate present in any one of the various metabolic pathways involved in cellular metabolism of bacteria, plants or animals. Small molecule analytes that can be analyzed using the methods of the invention also include bioorganic compounds associated with "natural products" chemistry including alkaloids, terpenoids, glycosides, phenols, phenazines, polylactoids and fatty acid synthase products.

Labeling Reaction

When the multifunctional labeling reagent takes the form of aniline or an aniline derivative, samples are preferably labeled at room temperature for about two hours in the presence of at least a 300-fold excess of aniline at about pH 4.5. While ambient temperatures are optimal, the labeling reaction can be conducted at a temperature as low as 15° C. to a temperature as high as 60° C., preferably a temperature that is between 20° C. and 30° C. While a pH of 4.5 is optimal, the labeling reaction can be conducted at a pHs as low as pH 3.0 or as high as pH 7.5, preferably a pH that is in between pH 4.0 and 6.0. Optionally, the labeling reaction is run in the presence of ethylcarbodiimide hydrochloride (EDC).

The samples are preferably complex mixtures. Advantageously, the GSIST method can be utilized with complex mixtures from various biological environments. A "biological environment" is to be broadly interpreted to include any type of biological system in which enzymatic reactions can occur, including in vitro environments, cell culture, cells at any developmental stage, whole organisms, organs, tissues, bodily fluids, and the like. For example, GSIST can be used for metabolic pathway analysis or to detect metabolites in regulatory flux in response to the application of a stimulus. Samples can be obtained from different organisms, cells, organs, tissues or bodily fluids. Samples can be obtained from prokaryotes or eukaryotes, including bacteria, yeast, fungi, protozoa, plants and animals. Changes in concentration of metabolites in an organisms, cell, organs, tissue or bodily fluid in response to a stimulus, treatment, exposure or other event can be analyzed.

Sample Analysis

GSIST allows for absolute quantification of known compounds as well as relative quantification of unknown compounds without requiring standards. Metabolites from control samples (relative quantification) or metabolite standards (absolute quantification) and experimental samples are derivatized with multifunctional isotopic variants that are chemically identical but isotopically distinct. The derivatized metabolites from both samples (experimental, and control/metabolite standard) are mixed, and each molecule from control or standard sample serves as an internal standard for determining the concentration of the chemically identical component in experimental sample. The mixture can be analyzed by any method that is capable of distinguishing analytes on the basis of mass. Mass spectrometric analysis can used to determine peak intensities and quantitate isotope ratios in the samples, determine whether there has been a change in the concentration of a metabolite or other small molecule analyte between two samples, and to facilitate identification of a metabolite or other small molecule analyte. Preferably, changes in metabolite concentration between the control and experimental samples are determined by electrospray ionization mass spectrometry (ESI-MS), but MALDI-MS may also be used.

The absolute quantification embodiment of GSIST makes use of prepared metabolite standards, but it differs fundamentally from the typical standard addition method. In the traditional standard addition method, the internal standards are chemically identical but isotopically different forms of the analyte to be analyzed. In other words, the labeled standards have the heavy isotope incorporated directly into the molecule at a position that is part of the normal molecular structure of the compound to be analyzed. This is why each isotopically labeled standard for standard addition has to be available independently. In the present invention, on the other hand, the heavy isotope is incorporated into the commercial standard during the process of sample preparation. It is added covalently by means of the derivatizing agent. Only one single isotopic labeling (derivatizing) agent needs to be available a priori for all analytes. The metabolite standard is isotopically labeled, post-synthesis, by way of chemical derivatization, not as part of the process of its initial synthesis. This means that the standards can all be synthesized normally, without incorporation of a heavy isotope. The heavy isotope is added to the standard by way of derivatization with the multifunctional heavy isotope labeling agent. Each different standard contains the same heavy isotope moiety added by the multifunctional isotope labeling agent. As a further advantage, the standards can be derivatized at the same time in the same mixture, to yield a mixture of isotopically labeled standards.

Notwithstanding the preceding, it should be noted that in GSIST, typically the control/standard sample is labeled with the heavy isotopic variant of the labeling agent, and the experimental sample is labeled with the light isotopic variant, this can be reversed such that the experimental sample is labeled with the heavy isotopic variant and the control/standard is labeled with the light isotopic variant.

For absolute quantification of metabolites using GSIST, unlabeled metabolite standards are synthesized or purchased. Although they may labeled individually, the standards can conveniently be mixed together and labeled simultaneously, typically with the heavy form of the labeling agent, for example $^{13}C_6$-aniline. This mixture of heavy isotope-labeled (i.e., derivatized) standards is the control sample. For metabolic pathway labeling, this control sample can contain many labeled metabolite standards, up to 20, 30, 40 or more. The experimental sample, e.g., a biological sample such as a cell lysate or a bodily fluid, is typically labeled with the light form of the labeling agent, for example $^{12}C_6$-aniline. After labeling, aliquots from the two samples are mixed at a specific ratio, with the control sample supplying the internal metabolite standards. The resulting mixture can be conveniently analyzed by mass spectrometry. Mass spectrometric analysis is useful to identify or quantify the small molecule analytes in the mixture as exemplified in the methods described below, and also exemplified in the methods described in U.S. Pat. No. 6,864,099 (Regnier, Mar. 8, 2005) and U.S. Pat. No. 6,872,575 (Regnier, Mar. 29, 2005) and US Pat. Pub. Nos. 20030186326 (Regnier et al., Oct. 2, 2003), 20080050827 (Mirzaei et al., Feb. 28, 2008) and 20080050833 (Smith et al., Feb. 28, 2008). Preferably, the mixture is analyzed using LC-MS, analogous to the global internal standard method (GIST) as described in detail in U.S. Pat. No. 6,864,099 (Regnier, Mar. 8, 2005) and U.S. Pat. No. 6,872,575 (Regnier, Mar. 29, 2005) and US Pat. Pub. No. 20030186326 (Regnier et al., Oct. 2, 2003). Briefly, the concentration of individual metabolites is determined from the ratio between the intensity of corresponding light (experimental) and heavy (standard) peaks in the doublet sets of ions.

A problem that can arise when using small molecule standards, as in the absolute quantification embodiment of the invention, relates to possible differences in the matrix or environment between the standards and the sample, which in turn results in different derivatization efficiency. The background matrix for a biological sample can be quite different from the background matrix for a mixture of metabolite standards prepared in the laboratory. To address this problem, the GSIST method optionally includes a refinement in the form of a quantification method referred to herein as Global Isotope-labeled Internal Standard Addition (GILISA). GILISA is shown schematically in FIG. 5. In GILISA, two aliquots of the experimental sample and a mixture of metabolite standards are prepared. To one aliquot of experimental sample is added a small amount of the metabolite standard mixture. Both aliquots are then derivatized with the light isotopic variant, e.g., aniline. The metabolite standard mixture is derivatized with the heavy isotopic variant, e.g., $^{13}C_6$-aniline, and then split into two aliquots in equal amount and added to the two light isotopically labeled experimental samples, which are analyzed through LC-MS. The metabolites can be quantified using the calculation formula provided in Example I.

Advantageously, in vitro derivatization with a multifunctional reagent such as an aniline-based reagent as described herein allows for comparative analysis the metabolites or other small molecule analytes in multiple samples even in the absence of synthetic isotopically labeled (e.g., $^{13}C$-coded) metabolite standards. Relative quantification of metabolites using GSIST can be achieved by comparing the concentration of metabolites in a first biological sample (referred to herein as a reference or control sample) obtained or produced under one set of biological conditions, with the concentration of metabolites in a second biological sample (referred to herein as an experimental sample) obtained or produced under a different set of conditions. The first and second samples are labeled with the heavy and light forms of the multifunctional isotopic labeling agent, or example $^{13}C_6$-coded and non-$^{13}C_6$-coded aniline, respectively. The two labeled samples are mixed in defined ratios, preferably equal amounts (1:1). The combined sample is subjected to mass spectrometric analysis, preferably LC-MS.

In a complex combined mixture, there may be many metabolites or small molecule analytes that will not change in concentration between the control or reference sample, and one or more experimental samples. The metabolites whose levels are unchanged are used to establish the normalized isotope ratio for metabolites that did not change in concentration. During mass spectrometric analysis, a normalized isotope ratio characterizing metabolites (or other small molecule analytes) whose concentration is the same in the first and second samples is first determined, then the isotope ratio of the first and second isotopically labeled metabolites is determined and compared to the normalized isotope ratio. A difference in the isotope ratio of the first and second isotopically labeled metabolites and the normalized isotope ratio is indicative of a difference in concentration of the metabolite in the first and second samples.

In another aspect, the invention provides a method for directly identifying a metabolite or other small molecule analyte in a sample. The sample is divided into first and second portions. A first isotopic variant of a labeling reagent is contacted with each said metabolite in the first portion to yield one or more first isotopically labeled metabolites. The method is not limited to any particular labeling agent. The labeling agent can, for example, be specific for one functional group, such as 3-carbinol-1-methylpyridinium iodide (CMP) or N-alkyl-4-aminomethyl-pyridinum iodide, which label carboxylic acids (Yang et al., Electrophoresis 2008, 29:4549-4560), or it can label more than one functional group, such as an N-hydroxysuccinimide ester of N-alkylnicotinic acid (Cn-NA-NHS) which can N-acylate an amino acid (Yang et al., 2006, Anal. Chem., 78:4702-4708; Regnier et al., PCT Publication WO2007/117665, published Oct. 18, 2007), or react with a phenolic hydroxyl (Yang et al., 2008, J Chromatog B, 870:233-240). Aniline and the other multifunctional labeling reagents described herein are additional examples of labeling agents that can be used. A second isotopic variant of the labeling reagent is contacted to each said metabolite in the second portion to yield one or more second isotopically labeled metabolites, wherein the first and second isotopically labeled analytes are chemically equivalent yet isotopically distinct. Aliquots, preferably equal aliquots, from the first and second samples are combined. The combined sample is subjected to mass spectrometric analysis to yield m/z values for at least one metabolite. The m/z values are then compared to known or predicted m/z values for a known analyte (e.g., compared against a database of m/z values) to identify the metabolite. Example IV shows an application of this method utilizing GSIST to identify ganoderic acids in mushroom extracts. Advantageously, it is possible to determine how many functional groups on the metabolite were labeled, making it possible to rule out known metabolites with a higher or lower number of functional groups. For example, an amu difference of 6 amu when aniline and $^{13}C_6$-aniline are used indicates one functional group; a difference of 12 amu indicates two functional groups, and so on.

The present invention is illustrated by the following examples. It is to be understood that the particular examples, materials, amounts, and procedures are to be interpreted broadly in accordance with the scope and spirit of the invention as set forth herein.

Example I

Simultaneous Quantification of Metabolites Involved in Central Carbon and Energy Metabolism Using Reverse Phase Liquid Chromatography-Mass Spectrometry and In Vitro $^{13}C$ Labeling Comprehensive analysis of intracellular metabolites is a critical component of elucidating cellular processes. Although the resolution and flexibility of reversed phase liquid chromatography-mass spectrometry (RPLC-MS) makes it one of the most powerful analytical tools for metabolite analysis, the structural diversity of even the simplest metabolome provides a formidable analytical challenge.

Here we describe a robust RPLC-MS method for identification and quantification of a diverse group of metabolites ranging from sugars, phosphosugars, and carboxylic acids to phosphocarboxylic acids, nucleotides and co-enzymes. This method is based on in vitro derivatization with a $^{13}C$-labeled tag that allows internal standard based quantification and enables separation of structural isomer pairs like glucose 6-phosphate and fructose 6-phosphate in a single chromatographic run. Calibration curves for individual metabolites showed linearity ranging over more than two orders of magnitude with correlation coefficients of $R^2>0.9975$. The detection limits at a signal-to-noise ratio of 3 were below 1.0 µM (20 pmol) for most compounds. Thirty common metabolites involved in glycolysis, the pentose phosphate pathway, and tricarboxylic acid cycle were identified and quantified from yeast lysate with a relative standard deviation of less than 10%.

We report a new post-biosynthetic (in vitro) stable isotope encoding procedure called Group Specific Internal Standard Technology (GSIST) (Yang et al., *Analytical Chemistry* 2008, 80: 9508-9516; Sedlak et al., "In vitro $^{13}C$ labeling for simultaneous identification and quantification of central carbon intermediates in genetically modified *Saccharomyces* yeast capable of glucose/xylose co-fermentation using reverse phase liquid chromatography-mass spectrometry," Poster 2-38. 30$^{th}$ *Symposium on Biotechnology for Fuels and Chemicals*, (Society for Industrial Microbiology) New Orleans, La.: May 4-7, 2008). In GSIST, metabolites from control samples (or metabolite standards) and experimental samples are derivatized with chemically identical but isotopically distinct labeling agents. In effect, sample components are chemically coded according to their sample origin. After mixing these derivatized metabolites, each molecule from the control or standard sample serves as an internal standard for determining the concentration of the corresponding compounds in the experimental sample. Recent studies in our laboratory have focused on derivatizing agents targeting primary amines (Jensen et al., *Biotechnol Bioeng* 1999, 63:356-362) and carboxyl groups (Yang et al., *Analytical Chemistry* 2007, 79:5150-5157). Although these coding agents work well for specific classes of molecules, they have some limitations in global and pathway targeted approaches since not all molecules contain the same functional groups. For this reason we have introduced a new derivatization reagent targeting multiple functional groups that is more suitable for quantification of specific metabolic pathways as well as differential global metabolomics. An in vitro aniline derivatization is used that allows for absolute quantification of known compounds or relative quantification of unknown compounds without requiring standards. Moreover large numbers of analytes can be analyzed in a single LC-MS run.

The utility of in vitro aniline derivatization was investigated in connection with the quantification of intermediates in central carbon and energy metabolism. Among the whole cellular metabolic network, central carbon metabolism, composed of glycolysis, the pentose-phosphate pathway, and the tricarboxylic acid cycle (TCA), plays a key function in substrate degradation, energy and cofactor regeneration, and biosynthetic precursor supply. There are more than 35 intermediates that belong to several categories of chemical compounds: phosphorylated sugars, phospho-carboxylic acids, carboxylic acids, nucleotides and co-factors. Simultaneous analysis of these compounds is a challenging analytical problem. Here we describe a new in vitro $^{13}C_6$ labeling method that allows accurate determination of most intermediates involved in central carbon and energy metabolism in a single 30 minute reversed-phase liquid chromatography-mass spectrometry (RPLC-MS) run.

MATERIALS AND METHODS

Materials and Reagents

All metabolite standards, aniline, aniline-$^{13}C_6$, N-(3-dimethylaminopropyl)-N'-ethylcarbodiimide hydrochloride (EDC), tributylamine (TBA), triethylamine (TEA) and HPLC grade water were purchased from Sigma-Aldrich (St. Louis, Mo.). HPLC grade acetonitrile (CAN) was obtained from Mallinkrodt Baker (Phillipsburg, N.J.).

Yeast Growth and Fermentation

*Saccharomyces cerevisiae* 424A(LNH-ST), a derivative of *S. cerevisiae* ATCC 4124 (Ho et al., *Advances in Biochemical Engineering-Biotechnology* 1999 65:163-92; Ho et al., *Appl Environ Microbiol* 1996 64:1852-1859) was inoculated directly from the agar plates into 5 ml of YEP+2% glucose medium. The cultures were incubated in a shaker at 30° C. and 200 rpm and grown aerobically overnight. The following morning, the culture were transferred directly to 100 mL YEP+2% glucose in a 300 mL Erlenmeyer flask equipped with a sidearm (Bellco), which allows for direct monitoring of the growth of yeast cultures by a Klett colorimeter (Manostat Corp.). The cultures were incubated as described above until cell density reached 500 KU. At this point, 24 mL of (50%) glucose were added to the flask. The flask was then sealed with Saran wrap to allow fermentation to proceed under largely anaerobic conditions. The cultures were incubated as described above and cell growth monitoring by Klett colorimeter. One mL samples of the mixture were removed at proscribed intervals to monitor fermentation. The sample for intracellular metabolite analysis was taken 3 hours after fermentation started. Glucose and fermentation products such as glycerol, acetic acid, and ethanol were analyzed by high performance liquid chromatography (HPLC) using HPX 87H (8×300 mm, Bio-Rad Laboratories, Calif.).

Sample Preparation

Sampling was performed as described by Gonzales (Gonzalez et al., *Yeast* 1997, 13:1347-1355) and Lange (Lange et al., *Biotechnology & Bioengineering* 2001, 75:406-415). Briefly, 5 mL of yeast culture was sprayed into 50 mL centrifugation tubes (Oak Ridge centrifugation tube, FEP) containing 26 mL of cold solution with 60% (v/v) analytical grade methanol (Mallincrodt), kept at −45° C. in the cryostat bath (HAAKE Phoenix II P1). After 3 min in −45° C. in the cryostat bath, the mixture was centrifuged at 500×g for 5 min in a Beckman Avanti J-301 set at −20° C., supernatant was discarded and the cell pellet resuspended in 5 mL of cold quenching solution (−45° C.) followed by a second identical centrifugation. Tubes containing washed pellets were kept at −45° C. in the cryostat bath. The metabolites were extracted from cell pellets with boiling ethanol. Tubes containing cell pellets were placed into a 90° C. waterbath and immediately overlain by a solution of 75% (v/v) boiling 100% ethanol, vortexed, and kept for 3 min in a 90° C. water bath. After 3 min the tubes were placed into a −80° C. freezer.

LC-MS

The HPLC/ESI MS system consisted of a capillary HPLC system (1100 Series LC, Agilent) and an electrospray ionization (ESI) source of time-of-flight (TOF) mass spectrometer (MSD TOF, Agilent). The system was controlled by ChemStation software (Agilent). The autosampler was set at 10° C. Separations were performed on a Zorbax C8 column (2.1 mm×150 mm, Agilent). The elution started from 95% mobile phase A (5 mM TBA aqueous solution, adjusted to pH 5.0 with acetic acid) and 5% mobile phase B (100% ACN), raised to 70% B in 25 min, further raised to 100% B in 2 min, and then held at 100% B for 3 min. The flow rate was set at 0.3 mL/min with injection volume as 20.0 µL. The column was preconditioned by pumping the starting mobile phase mixture for 10 min. LC-ESI-MS chromatograms were acquired in negative ion mode under the following conditions: capillary voltage of 4000 V and fragmentor of 165 V, dry temperature at 300° C., dry gas flow maintained at 8.0 L/min, and an acquisition range of m/z 150-1000.

General Labeling Protocol

A solution of 3.0 M aniline or aniline-$^{13}C_6$ was prepared in water and titrated by 6 M hydrochloric acid to pH 4.5. EDC at 20.0 mg/mL was prepared freshly in water. A 100 µL working or sample solution was added with 10 µL of 3.0 M aniline or aniline-$^{13}C_6$, followed by adding 10 µL of 200.0 mg/ml EDC (~5 µmol). The mixture was vortexed and then incubated with gently shaking at ambient temperature (~22° C.) for 2 hours. The labeling reaction was stopped by adding 2 µL of triethylamine.

Method Evaluation and Validation

Stock solutions for each standard were prepared in water at 10 mM. Individual standard metabolite solutions (each 0.1 mM) were separately labeled with aniline and aniline-$^{13}C_6$, and a 1:1 mixture analyzed. The LC peak and MS spectrum patterns were examined to confirm the labeling reaction and to gain the m/z value for sample analysis. A 14.3 µM standard mixture including 33 analytes was prepared from the stock solutions and used for optimizing the labeling and separation conditions. To determine the detection limit and linearity range, a mixture of 33 analytes at various concentrations for each component (depending on their MS response intensity) were prepared. A series of dilutions from this mixture were labeled with aniline. Another aliquot of this mixture was labeled with aniline-$^{13}C_6$, and a certain amount of this derivative mixture added into the above series of solutions as references for MS response calibration.

RESULTS AND DISCUSSION

Labeling Strategy

The compounds directly involved in central carbon metabolism contain carbonyl, phosphate and carboxyl groups. It was our intent to develop a relatively global labeling approach which could introduce $^{13}$C-coded hydrophobic moieties into all analytes of interest and allow us to determine all these compounds in a single RPLC-MS run. Reductive amination with amine-containing reagent is a common way to label carbonyl groups (Baxter and Reitz, *Organic Reactions* 2002, 59:1-714). Amine-containing reagents have also been reported to label carboxyl and phosphate groups by nucleophilic addition using a water soluble carbodiimide such as EDC (Ford et al., *J Chromatogr A* 2007, 1145:241-245; Ivanovskaya et al., *Nucleosides & Nucleotides* 1987, 6:913-934). Based on these observations, isoforms of aniline (including aniline-$^{13}$C$_6$) were selected for experiments in isotope coding based on the reactions seen in FIG. 1.

Optimization of Derivatization Reaction

Following optimization of reaction conditions, phosphomonoesters were labeled with aniline at 20° C. and pH 4.5-5.5 for 1 hour using EDC catalysis (Ivanovskaya et al., *Nucleosides & Nucleotides* 1987, 6:913-934). These conditions are similar to those used in primary amine labeling of carboxyl groups using EDC (Ford et al., *J Chromatogr A* 2007, 1145:241-245). On the other hand, carbonyl labeling with primary amines is typically carried in a nonaqueous solvent such as methanol with ~30% acetic acid at roughly 50° C. Because the intermediate Schiff base formed in carbonyl labeling is unstable under acidic conditions, it is then generally reduced with NaCNBH$_3$ to form a stable secondary amine. We reexamined these conditions and found that the labeling conditions for phosphate and carbonate, namely pH 4.5 and room temperature, also worked well for glucose, xylose and phosphosugars. Carbonyl groups in glucose, xylose, and phosphosugars were derivatized under these conditions even without the addition of acetic acid. Inclusion of acid in the reaction possibly converts ketoses to aldoses, but was found to bring no advantage here because the Schiff base intermediate is unstable at pH 4.5. In fact, adjusting the pH to 10 by adding 2 μL of TEA at the conclusion of labeling, appreciably increased stability. No significant degradation was observed over 3 days when a labeled sample was placed in the autosampler at 10° C. Addition of NaCNBH$_3$ was also investigated, and the overall LC separation deteriorated with the use of this reagent. Therefore, this reduction step was omitted.

Aniline concentrations from 0.3 M to 6 M were used to further optimize the primary labeling conditions above using extracted ion chromatographic peak intensity. With increasing concentration, labeling yield increased especially for carbonyl-containing analytes and some carboxylic acids, such as succinic and fumaric acid. Labeling time was examined from 10 min to 150 min. The yield was roughly 70% in 10 min and slowly increases to nearly quantitative derivatization at 105 min where most unlabeled analytes were below 0.1%. Raising labeling temperature from ambient to 50° C. decreased labeling, probably owing to acceleration of EDC hydrolysis. The final optimized protocol is to label at ambient temperature for 2 hours with at least a 300-fold excess of aniline at pH 4.5.

Optimization of Analytical Conditions

Labeled standards were analyzed by ion pairing RPLC followed by ESI-MS in the negative ion mode of ionization. TBA was adapted as an ion pairing agent because of its promising performance in the separation of unlabeled central carbon metabolites (Luo et al., *J Chromatogr A* 2007, 1147:153-164). Optimization of the separation focused on mobile phase pH and TBA concentration. A pH of 5.0 was found to be the optimum for all the analytes. To shorten analysis time, 5 mM TBA was used.

Figure 2:
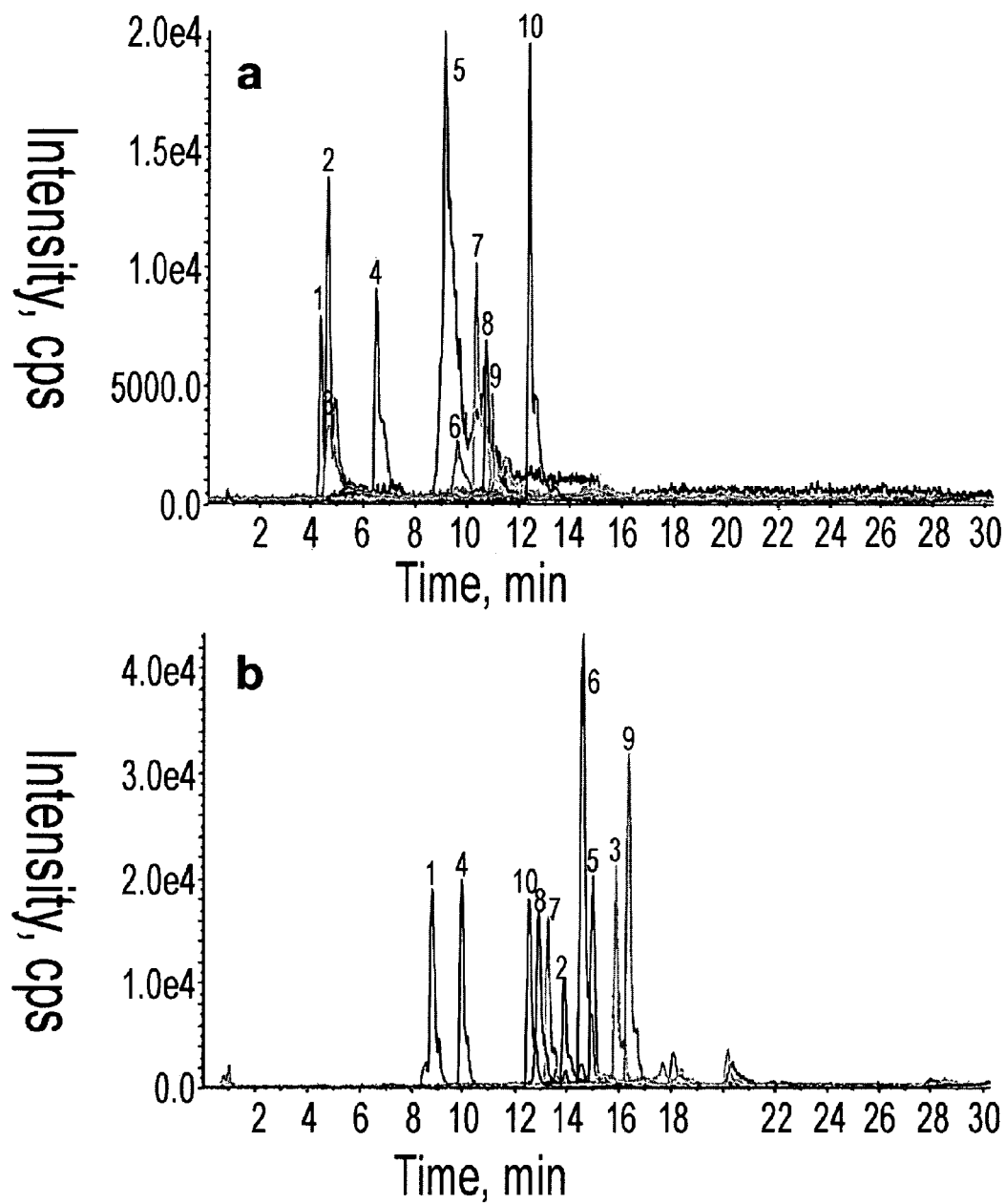
FIG. 2 shows RPLC-MS performance comparison for 12.0 µM free (a) and aniline-labeled (b) metabolites. Metabolites: 1. glucose 6-phosphate; 2. fructose 6-phosphate; 3. D-erythrose 4-phosphate; 4. Adenosine 5-monophosphate; 5. malate; 6. ketoglutarate; 7. gluconate 6-phosphate; 8. fructose 1,6-bisphosphate; 9. phospho(enol)pyruvate; 10. flavin adenine dinucleotide (reference peak). LC-MS conditions were described in the method section.

Analytical performance enhancement of several representative labeled metabolites is demonstrated in FIG. 2. Note that there is no significant variation from FIGS. 2a to 2b in peak intensity and retention time of reference peak 10. It is concluded that labeling improved the separation in terms of peak shape, resolution, and selectivity, and also enhanced MS sensitivity. The change of separation selectivity is obviously attributed to different labeling patterns of the isomers, such as glucose 6-phosphate and fructose 6-phosphate, which will be discussed further below. The enhancement in peak intensity results from the increase in analyte hydrophobicity after labeling (Yang et al., *Analytical Chemistry* 2006, 78:4702-4708).

Method Evaluation

Most metabolites studied here have more than one functional group which could be labeled. To validate the labeling reaction, standard metabolites were individually labeled with aniline and aniline-$^{13}$C$_6$. A mixture of equal amounts of the two labeled solutions was analyzed. Labeling patterns can be easily recognized by examining the spectrum. Chromatographic peaks should contain a doublet set of ions, e.g. two major ions of similar peak intensity and a mass difference of 6n (n=1, 2, 3) where n is the number of functional groups in the molecule that were labeled. Also, the m/z of the first ion in the doublet should be the molecular weight of the metabolite plus 75 amu×n (n=1, 2, 3). Retention time, labeling pattern, and MS species identified are summarized in Table 1.

TABLE 1

Labeling and identification RPLC-MS results of standard metabolites

| Peak No. | Compound | Retention time (min) | m/z value $^{12}$C labeling | m/z value $^{13}$C labeling | Non-labeling | Labeling pattern | MS species |
|---|---|---|---|---|---|---|---|
| 1 | Glycerol 3-phosphate | 4.60 | | | 152.99 | Non- | [M − H$_2$O − H]$^-$ |
| 2 | Xylose | 4.96 | 260.07 | 266.09 | | Mono- | [M + Cl]$^-$ |
| 3 | NAD | 5.01 | | | 698.08 | Non- | [M + Cl]$^-$ |
| 4 | Glucose | 5.27 | 290.08 | 296.10 | | Mono- | [M + Cl − H]$^-$ |
| 5 | Fructose 6-phosphate | 8.81 | 334.07 | 340.09 | | Mono- | [M − H]$^-$ |
| 6 | Lactic acid | 8.93 | 164.07 | 170.09 | | Mono- | [M − H]$^-$ |
| 7 | D-Ribulose 5-phosphate | 9.37 | 304.06 | 310.08 | | Mono- | [M − H]$^-$ |
| 8 | AMP | 9.97 | 421.10 | 421.12 | | Mono- | [M − H]$^-$ |

TABLE 1-continued

Labeling and identification RPLC-MS results of standard metabolites

| Peak No. | Compound | Retention time (min) | $^{12}$C labeling | $^{13}$C labeling | Non-labeling | Labeling pattern | MS species |
|---|---|---|---|---|---|---|---|
| 9  | Dihydroxyacetone 1-P      | 10.07 | 244.04 | 250.06 |        | Mono- | $[M - H]^-$ |
| 10 | NADP                      | 10.31 |        |        | 724.06 | Non-  | $[M - H]^-$ |
| 11 | D-(-)Glycerate 3-P        | 11.94 | 242.03 | 248.06 |        | Mono- | $[M - H]^-$ |
| 12 | FAD                       | 12.56 |        |        | 784.15 | Non-  | $[M - H]^-$ |
| 13 | ADP                       | 12.56 | 501.07 | 507.03 |        | Mono- | $[M - H]^-$ |
| 14 | Fructose 1,6-bisphosphate | 12.93 | 396.03 | 402.05 |        | Mono- | $[M - H]^-$ |
| 15 | Gluconate 6-phosphate     | 13.29 | 425.11 | 437.15 |        | Bi-   | $[M - H]^-$ |
| 16 | Glucose 6-phosphate       | 13.90 | 409.12 | 421.16 |        | Bi-   | $[M - H]^-$ |
| 17 | NADH                      | 14.16 | 633.11 | 639.13 |        | Mono- | $[M - \text{nicotinamide} + H_2O-]^-$ |
| 18 | Ketoglutarate             | 14.61 | 295.01 | 307.14 |        | Bi-   | $[M - H]^-$ |
| 19 | DL-Glyceraldehyde 3-P     | 14.99 | 319.09 | 331.13 |        | Bi-   | $[M - H]^-$ |
| 20 | Malate                    | 15.01 | 283.11 | 295.15 |        | Bi-   | $[M - H]^-$ |
| 21 | ATP                       | 15.14 | 581.03 | 587.05 |        | Mono- | $[M - H]^-$ |
| 22 | D-Ribose 5-phosphate      | 15.25 | 379.11 | 391.15 |        | Bi-   | $[M - H]^-$ |
| 23 | Acetyl Co A               | 15.69 |        |        | 790.11 | Non-  | $[M - H]^-$ |
| 24 | D-Erythrose 4-phosphate   | 15.88 | 349.09 | 361.13 |        | Bi-   | $[M - H]^-$ |
| 25 | Phospho(enol)pyruvate     | 16.38 | 317.07 | 329.11 |        | Bi-   | $[M - H]^-$ |
| 26 | Succinate                 | 16.43 | 267.12 | 279.16 |        | Bi-   | $[M - H]^-$ |
| 27 | NADPH                     | 16.47 | 695.07 | 701.09 |        | Mono- | $[M - \text{nicotinamide} - H]^-$ |
| 28 | Fumarate                  | 17.72 | 265.09 | 277.13 |        | Bi-   | $[M - H]^-$ |
| 29 | Glycerate 1,3-bisphosphate| 17.99 | 490.09 | 508.15 |        | Tri-  | $[M - H]^-$ |
| 30 | Oxalacetate               | 19.70 | 280.98 | 293.02 |        | Bi-   | $[M - H]^-$ |
| 31 | isocitrate                | 20.14 | 398.15 | 416.21 |        | Tri-  | $[M - H]^-$ |
| 32 | Citrate                   | 21.19 | 416.16 | 434.22 |        | Tri-  | $[M - H]^-$ |
| 33 | Cis-aconitate             | 22.35 | 380.98 | 399.04 |        | Tri-  | $[M - H_2O - H]^-$ |

Some special cases need to be addressed. Since simple labeled sugars are neutral, their chloride adducts were found by negative ESI-MS. Instead of aniline-labeling, the dehydrated glycerol 3-P ion was found. This ion probably arose by intermolecular addition of a hydroxyl group at C-1 that attached the EDC-activated C3-phosphate. Phosphoaldoses such as glucose 6-phosphate and ribose 5-phosphate were bis-labeled while phosphoketoses such as fructose 6-phosphate and ribulose 5-phosphate were mono-labeled. This illustrates that ketoses do not convert to aldoses in the weak acid media. This labeling pattern benefits the separation of these isomers. They are easily separated without the need to fine tune the separation. NADH and NADPH were labeled, but with loss of the nicotinamide moiety. It is unclear whether this loss is due to in-source fragmentation or the labeling process itself On the other hand, oxidized forms of the coenzymes NAD, FAD, and NADP, were not labeled and quantification had to be performed by standard addition. It is presumed this is because of the formation of an intramolecular salt between the quaternary amine on the pyridine ring and the negatively charged phosphate group. In cases where multiple phosphates exists within in a molecule, only one phosphate group was labeled, such as with fructose 1,6 bisphosphate, ADP, and ATP. On the basis of sensitivity, this method failed to analyze pyruvate.

Figure 3:
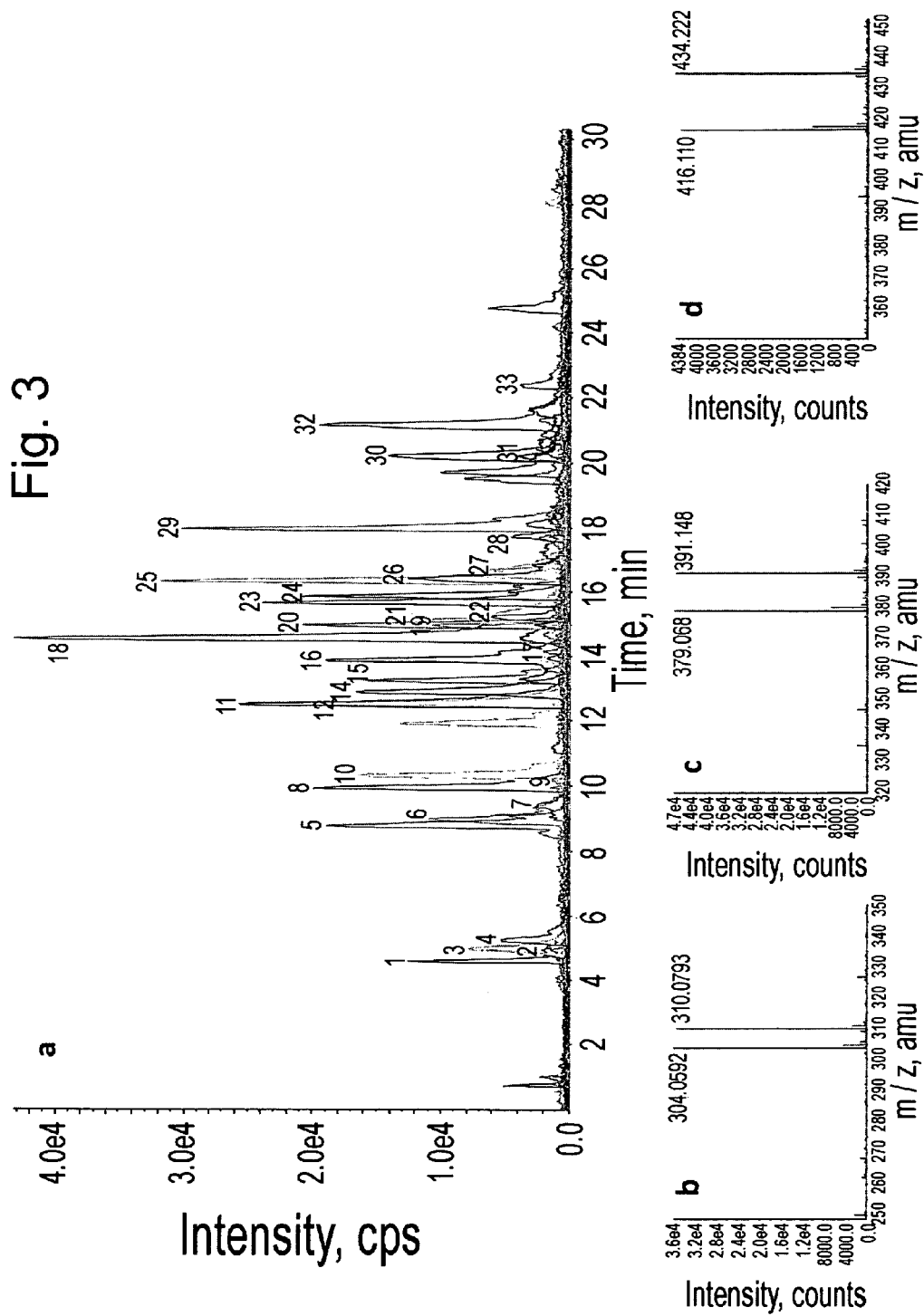
FIG. 3 shows overlapped extracted ion chromatograms of 33 metabolites in a 14.3 µM standard mixture. Peak identification is given in Table I. LC-MS conditions were described in the method section (a). Representative MS doublets from aniline-labeled and aniline-$^{13}C_6$-labeled metabolites which are mixed at 1:1 ratio: D-ribulose 5-phosphate-momo-aniline (b); D-ribose 5-phosphate-bis-aniline (c); citrate tri-aniline (d).

FIG. 3a shows overlapped extracted ion chromatograms from an equimolar mixture of 33 metabolites in which individual components were present at 14.3 μM. While some of components co-elute, they differ in m/z values and are easily differentiated. Some representative MS spectra with doublet ions are shown in FIG. 3b-d, giving further confirmation of labeling patterns. Clearly, subsequent to labeling RPLC-MS discriminated between 33 central carbon intermediates within 30 min.

Method Validation

The method was validated by determination of limit of detection (LOD), limit of quantification (LOQ), linearity range correlation coefficient and within-assay precision for the 33 analytes by analyzing aniline-labeled standard mixtures of variable concentration spiked with a constant amount of the same aniline-$^{13}C_6$-labeled standards (Table 2). For most compounds, the LOD (S/N=3) and LOQ (S/N=10) were established below 1.0 μM and 2.5 μM, respectively. The 3-phosphoenol pyruvate LOD was one of the lowest at 0.09 μM with a 20 μL injection volume. Somewhat higher LODs were observed for some intermediates, such as ribulose 5-phosphate and dihydroxyaceton 1-phosphate. Calibration curve for each compound was computed by plotting the peak intensity ratios between variable (light) and constant (heavy) amount of standard versus the additive nominal concentrations. Linearity was calculated using non-weighted last squared linear regression method and generally spanned 2 to 3 orders of magnitude with correlation coefficients higher than 0.995. A linear regression of all compounds showed a unit slope with interception close to zero (data not shown). Analytical precision was calculated from within-assay variability by measuring the peak intensity ratio of the analyte to its $^{13}C_6$-reference at a concentration ratio of 1:1, and expressed as the percentage relative standard deviation. The variation was generally below 5%. This approach reflects variations from the whole process, including sample preparation, labeling and LC-MS analysis.

TABLE 2

Basic parameters of the method

| Peak No. | Compound | LOD ($\mu M$)[a] | LOQ ($\mu M$)[b] | $^{12}C:^{13}C$ linearity range[c] | $R^2$ | RSD (%, n = 5)[d] |
|---|---|---|---|---|---|---|
| 1 | Glycerol 3-phosphate[e] | 0.48 | 1.68 | N/A | N/A | N/A |
| 2 | Xylose | 2.51 | 7.88 | 1:1~1/240:1 (1.00) | 0.9968 | 5.08 |
| 3 | NAD[e] | 0.77 | 2.40 | N/A | N/A | N/A |
| 4 | Glucose | 1.15 | 3.97 | 1:1~1/240:1 (0.80) | 0.9972 | 4.79 |
| 5 | Fructose 6-phosphate | 0.31 | 1.03 | 1:1~1/800:1 (0.26) | 0.9955 | 1.21 |
| 6 | Lactic acid | 0.57 | 1.93 | 1:1~1/800:1 (0.80) | 0.9984 | 1.10 |
| 7 | D-Ribulose 5-phosphate | 2.51 | 8.51 | 1:1~1/400:1 (1.00) | 0.9977 | 3.23 |
| 8 | AMP | 0.30 | 1.04 | 1:1~1/800:1 (0.26) | 0.9958 | 0.89 |
| 9 | Dihydroxyacetone 1-P | 2.50 | 8.23 | 1:1~1/400:1 (1.00) | 0.9965 | 4.12 |
| 11 | D-(−)Glycerate 3-phosphate | 0.47 | 1.45 | 1:1~1/800:1 (0.40) | 0.9988 | 1.35 |
| 12 | FAD[e] | 0.31 | 1.04 | N/A | N/A | N/A |
| 13 | ADP | 0.28 | 0.98 | 1:1~1/800:1 (0.26) | 0.9980 | 1.02 |
| 14 | Fructose 1,6-bisphosphate | 0.35 | 1.17 | 1:1~1/600:1 (0.26) | 0.9966 | 2.38 |
| 15 | Gluconate 6-phosphate | 0.35 | 1.22 | 1:1~1/800:1 (0.26) | 0.9954 | 2.17 |
| 16 | Glucose 6-phosphate | 0.41 | 1.37 | 1:1~1/800:1 (0.26) | 0.9969 | 2.93 |
| 17 | NADH | 2.51 | 9.03 | 1:1~1/400:1 (1.00) | 0.9972 | 4.29 |
| 18 | Ketoglutarate | 0.12 | 0.42 | 1:1~1/800:1 (0.26) | 0.9994 | 0.98 |
| 19 | DL-Glyceraldehyde 3-P | 0.55 | 1.80 | 1:1~1/600:1 (0.40) | 0.9981 | 3.97 |
| 20 | Malate | 0.30 | 1.06 | 1:1~1/800:1 (0.26) | 0.9975 | 2.15 |
| 21 | ATP | 0.55 | 1.77 | 1:1~1/600:1 (0.40) | 0.9983 | 1.17 |
| 22 | D-Ribose 5-phosphate | 0.62 | 2.05 | 1:1~1/800:1 (0.80) | 0.9979 | 3.01 |
| 23 | Acetyl Co A[e] | 0.24 | 0.86 | N/A | N/A | N/A |
| 24 | D-Erythrose 4-phosphate | 0.31 | 1.07 | 1:1~1/800:1 (0.26) | 0.9962 | 3.28 |
| 25 | Phospho(enol)pyruvate | 0.09 | 0.32 | 1:1~1/800:1 (0.26) | 0.9974 | 1.36 |
| 26 | Succinate | 0.46 | 1.55 | 1:1~1/800:1 (0.40) | 0.9955 | 3.45 |
| 27 | NADPH | 0.61 | 1.88 | 1:1~1/600:1 (0.40) | 0.9960 | 3.52 |
| 28 | Fumarate | 1.22 | 4.17 | 1:1~1/160:1 (0.80) | 0.9982 | 3.42 |
| 29 | Glycerate 1,3-bisphosphate | 0.19 | 0.66 | 1:1~1/800:1 (0.26) | 0.9963 | 1.71 |
| 30 | Oxal acetate | 0.55 | 1.75 | 1:1~1/320:1 (0.40) | 0.9978 | 4.42 |
| 31 | isocitrate | 1.30 | 4.47 | 1:1~1/320:1 (0.80) | 0.9957 | 3.99 |
| 32 | Citrate | 0.31 | 1.11 | 1:1~1/320:1 (0.40) | 0.9964 | 4.53 |
| 33 | Cis-aconitate | 1.32 | 4.77 | 1:1~1/320:1 (0.80) | 0.9976 | 4.65 |

[a]Based on peak intensity at S/N = 3
[b]Based on peak intensity at S/N = 10
[c]Concentration ratio between $^{12}C_6$-aniline-labeled and $^{13}C_6$-aniline-labeled analyte at the constant concentration of $^{13}C_6$-aniline-labeled analyte (indicated in the parenthesis).
[d]RSD is for the peak intensity ratio of the $^{12}C_6$-aniline-labeled to the $^{13}C_6$-aniline-labeled at the concentration ratio of 1:1
[e]Not labeled compounds This new concept of post-synthetic stable isotope method has many potential uses. It can be used for absolute quantification of any metabolite(s) and metabolite class(es) that contain carbonyl, phosphate and/or carbonate groups. It can also be used to identify unknown metabolites in complex samples (Example II) as well as global relative quantification (Example III).

Absolute Quantification of Metabolites Involved in Glycolysis, Pentose Phosphate Pathway, and TCA Cycle in Yeast Cell Extract

Figure 4:
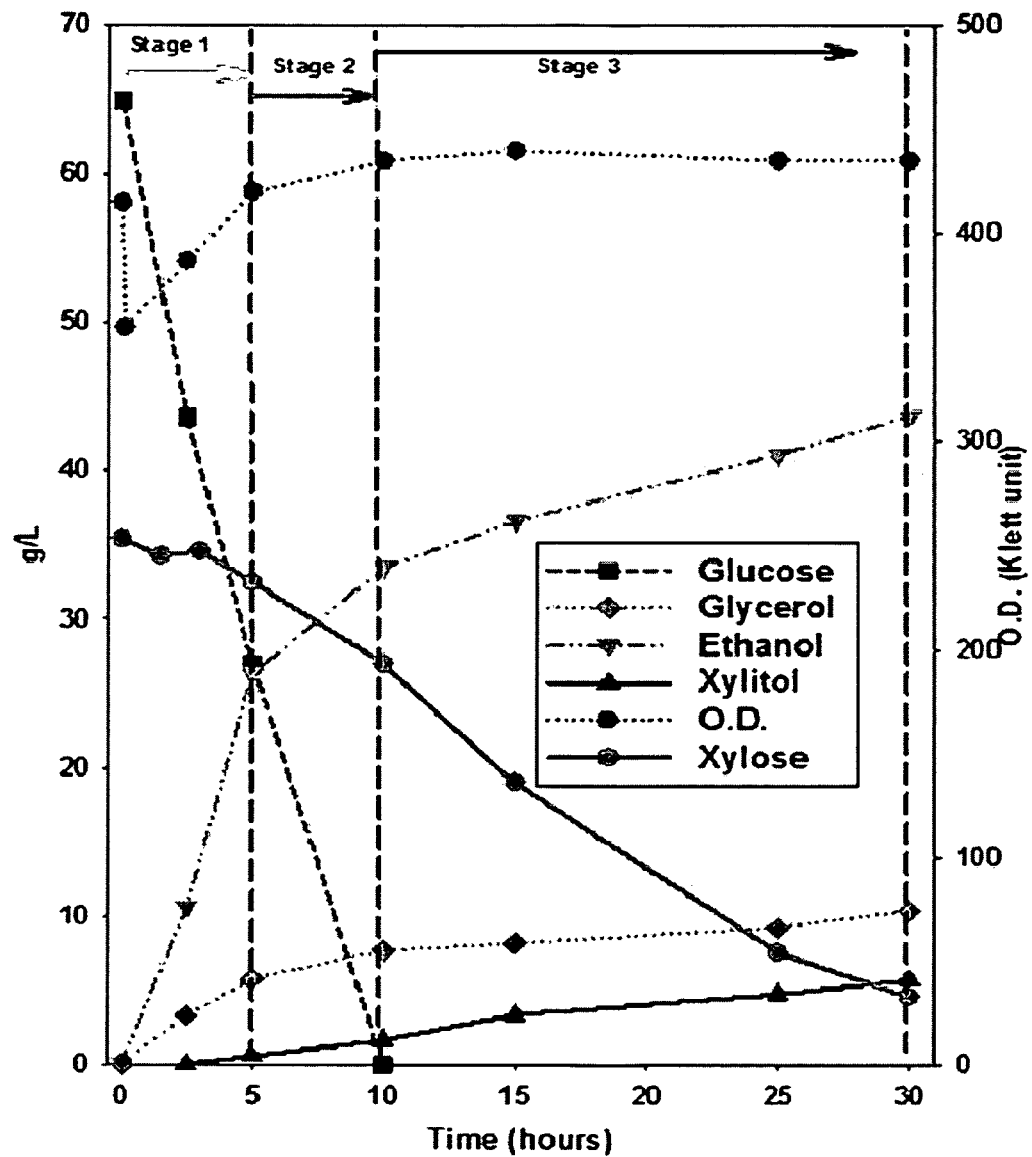
FIG. 4 shows a profile of glucose/xylose co-fermentation by recombinant yeast, *Saccharomyces cerevisiae* 424A (LNH-ST).

*S. cerevisiae* 424A(LNH-ST) is able to utilize glucose using the glycolytic pathway and xylose using the pentose phosphate pathway. FIG. 4 shows the typical profile of glucose/xylose co-fermentation. We used the GSIST method to evaluate 35 intermediates involved in yeast central carbon and energy metabolism. Due to unavailability of standards or structural analogues five metabolites could not be quantified. The rest of metabolites can be divided into the three categories based on the quantification approach.

Labeled Metabolites; Standards Available (Approach A—GILISA)—

Typically, GSIST quantification includes derivatization of sample and standard solutions with aniline and aniline-$^{13}C_6$, respectively. After labeling, mixtures of the sample and standards are mixed at a specific ratio and analyzed by LC-MS. The concentration of individual metabolites is then determined from the ratio between the intensity of corresponding light (sample) and heavy (standard) peaks in the doublet sets of ions. In this schema, however, the standards are labeled in a matrix that is different from the experimental sample matrix (i.e., the yeast extract). This may cause variation due to derivatization efficiency. A refinement of the GSIST method that would deal with this issue is a labeling and quantification schema referred to as Global Isotope-Labeled Internal Standard Addition (GILISA).

GILISA utilizes advantages of the standard addition method described by Vogt and others (Vogt et al., *Biochem Biophys Res Commun* 1998, 248:527-532; Finney et al., 2003, *Biochem Soc Trans* 31 (Pt 6): 1472-3; Sekiguchi et al., *J Chromatogr A* 2005, 1085:131-136).

The principle of GILISA is described in the equation $$V_x C_x / (V_x C_x + V_a C_a) = F_r I_{x+a} \quad \text{(Equation 1)}$$

where $C_x$ and $C_a$ are the concentration of the analyte and added standard, $V_x$ and $V_a$ are the volumes corresponding to the analyte and standard, $I_x$ and $I_{x+a}$ are the signal intensity of an unknown analyte and the signal intensity after addition, and $F_r$ is an instrument response factor. Typically the instrument response factor, $F_r$ is assumed to be 1 (Vogt et al., *Biochem Biophys Res Commun* 1998, 248:527-532; Huck et al., *Clin Chem* 2003, 49:1375-1380; Sekiguchi et al., *J Chromatogr A* 2005, 1085:131-136), i.e. there is no variation in instrument response between metabolites and standards. The exception to this would be when there is variable matrix suppression of ionization.

In GSIST, factor $F_r$ represents both instrument variation as well as the difference in derivatization efficiency and can be calculated when standards are added into two samples in equal concentration according to the equation. This is represented by the equation $$F_r = R_{x+a}/R_x \qquad \text{(Equation 2)}$$

where $R_x$ and $R_{x+a}$ represents signal intensity of the $^{13}$C-labeled standards in the $^{12}$C-labeled unknown sample and in the $^{12}$C-labeled unknown sample spiked with known amount of the standards, respectively. Combining Equations 1 and 2 produces the formula for GILISA where $C_x$ is the concentration of the unknown.

$$C_x = R_{x+a} I_x / (R_x I_{x+a} - R_{x+a} I_x)(V_a/V_x) C_a \qquad \text{(Equation 3)}$$

Figure 5:
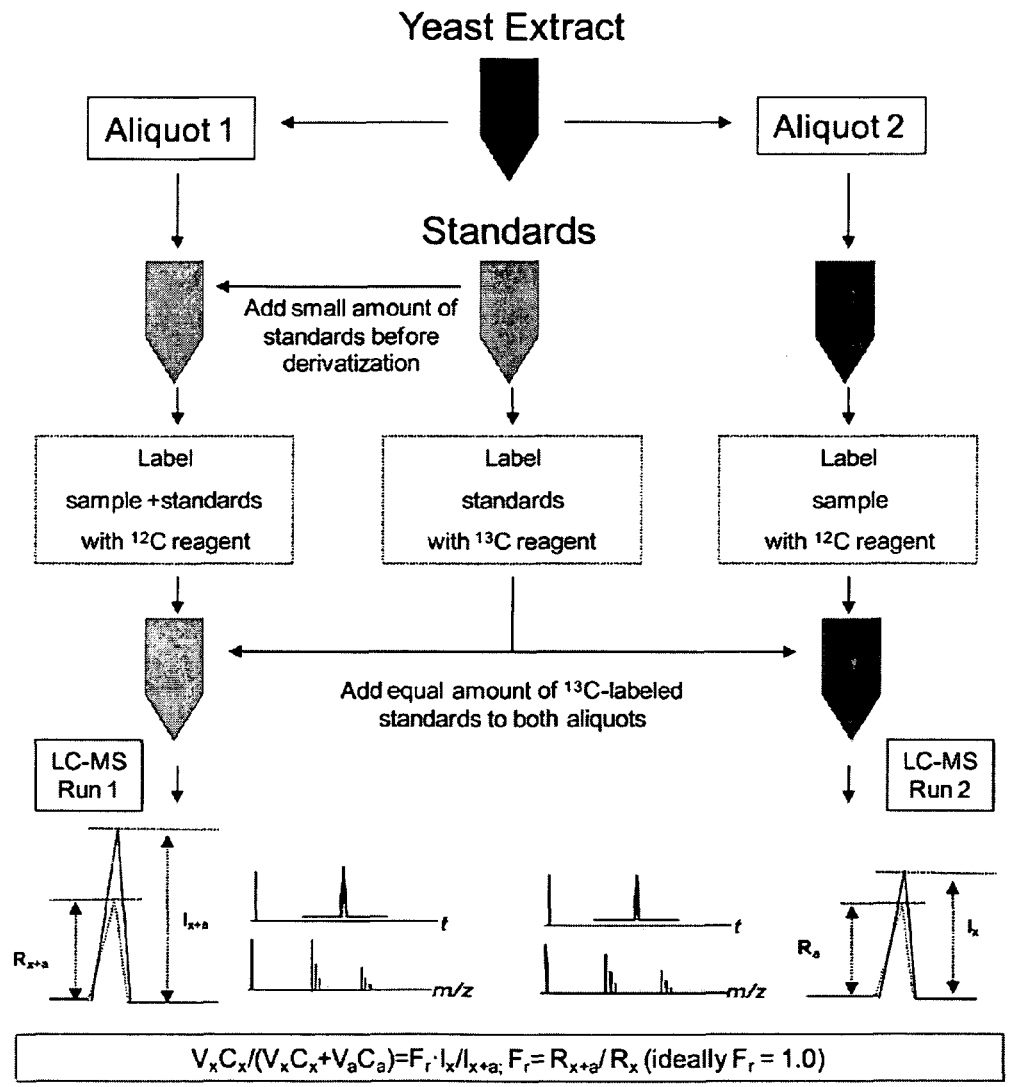
FIG. 5 shows a workflow for metabolite identification and quantification by GILISA.

The workflow for the method is described in FIG. 5. Two 100 μL-aliquots of yeast extract were taken to which 10 μL of 286 μmol/L standard mixture was added to one of them. These two aliquots were labeled with aniline. In the meantime, a 100 μL-aliquot of the standard mixture containing 14.3 μmol/L of each analyte was labeled with aniline-$^{13}$C$_6$. After labeling, 50 μL of this aniline-$^{13}$C$_6$-labeled standard mixture was added into the above two aniline-labeled samples. After LC-MS analysis, the quantification was achieved according to Equation 3.

Most of the intermediates in the cell extract were quantified using Approach A, but as noted some of the metabolites were not labeled or standards were not available.

Labeled Metabolites—Standards not Available (Approach B).

The metabolite D-6-phospho-glucono-δ-lactone was labeled in vitro, but no standard was available. A "labeled but no standard available approach" was used to quantify D-6-phospho-glucono-δ-lactone. Quantification of D-6-phospho-glucono-δ-lactone was based on the $^{13}$C-labeled standard of its contiguous peak, fructose 6-phosphate, which served as structural analogue.

Unlabeled Metabolites (Approach C).

Some of the metabolites could not be labeled by the aniline reagents, therefore their $^{13}$C-labeled standards are not available. These unlabeled metabolites were quantified by standard addition as described by Huck et al. (*Clin Chem* 2003, 49:1375-1380).

Figure 6:
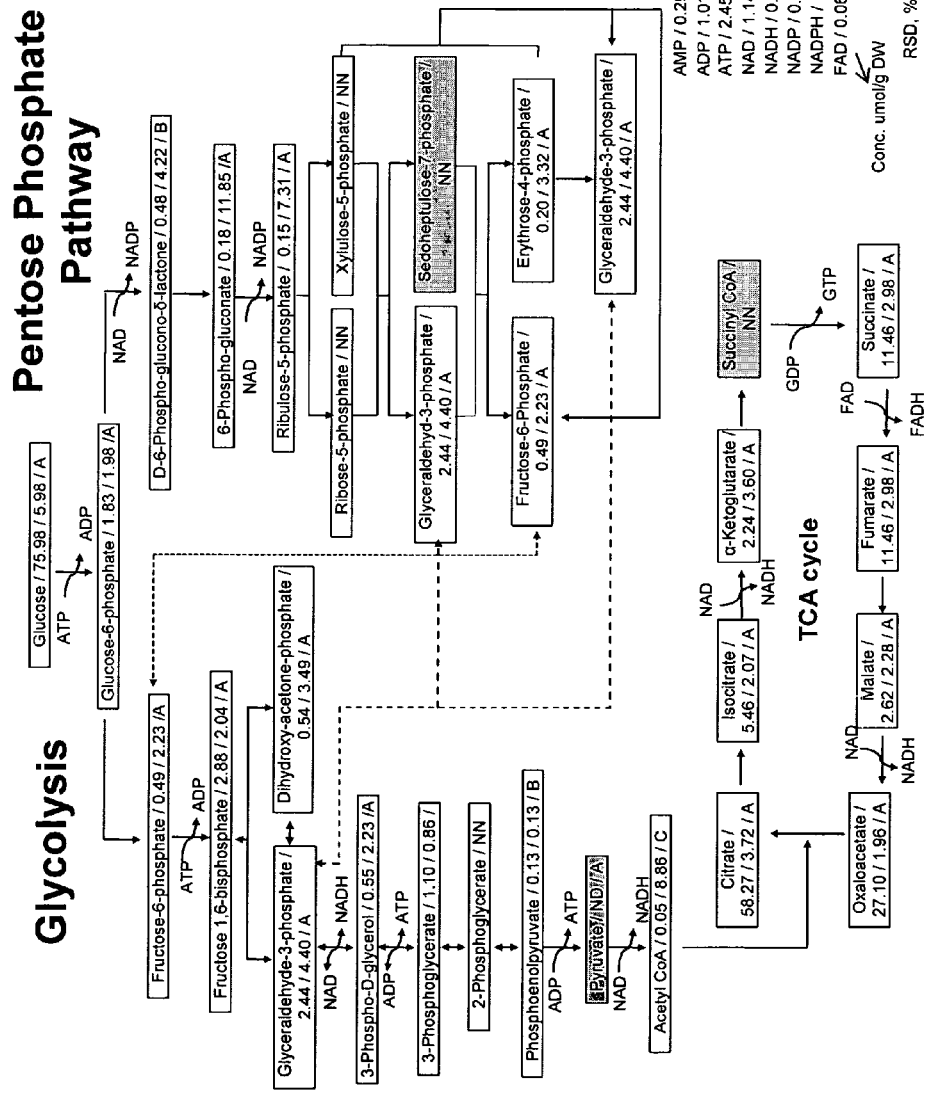
FIG. 6 shows a central carbon metabolism map and the determined metabolite concentration in yeast. Quantification approach using: A—GILISA, B—structural analogue, and C—Standard addition. NN—no standard available; ND—Not determined.

The quantification results of yeast central carbon and energy metabolism are summarized in FIG. 6. Generally, the RSD was below 10.0%.

CONCLUSIONS

Prior to the advent of metabolomics, classes of metabolites were generally examined individually as was the case with adenosine phosphate (Enrich et al., *J. Liq. Chromatogr. Relat. Technol.* 1999, 22:1391-1402), sugar phosphates (Smits et al., *Anal Biochem* 1998, 261:36-42; Huck et al., *Clin Chem* 2003, 49:1375-1380; van Dam et al., *Anal. Chem. Acta* 2002, 460:209-218; Sekiguchi et al., *J Chromatogr A* 2005, 1085: 131-136), or carboxylic acids from the TCA cycle (Kubota et al., *Biomed Chromatogr* 2005, 19:788-795; Masson et al., *J Chromatogr* 1991, 563:231-242; Tatar et al., *Microchem. J.* 1998, 58:306-314; Womersley et al., *J. Chromatogr.* 1985, 318:112-116; et al., *J Chromatogr A* 2001, 915:25-33). Though some methods worked on multiple classes (Piciore-anu et al., *J. Anal Chem* 2000, 72:2029-2034; Bhattacharya et al., *Anal Biochem* 1995, 232:98-106; Bajad et al., *J Chromatogr A* 2006, 1125:76-88), the coverage was not complete.

Among the numerous problems were that some unlabeled analytes showed little or no retention in RPLC. Another problem was that metabolite pools were highly complicated and some analytes were present in low abundance. Another complication was that some classes of analytes were structurally very similar and could not be differentiated by MS. Among the problem metabolites were glucose 6-phosphate and fructose 6-phosphate, ribose 5-phosphate and ribulose 5-phosphate, glyceraldehyde 3-phosphate and dihydroxyacetone phosphate, citrate and iso-citrate. The only way to differentiate between them was by chromatographic resolution, when possible. Still another issue was that $^{13}$C-labeled standards are not available for accurate MS-based quantification in some cases.

The intent in this work was to analyze multiple classes of intermediates, including nucleotides and cofactors, directly involved in central carbon metabolism by RPLC-MS in a single run. A robust RPLC-MS method is described here that allows accurate determination of essentially all the intermediates involved in central carbon metabolism in a single 30 min-run through in vitro labeling with isotopically distinguishable coding agents (FIG. 6). The only exception was pyruvate. In vitro isotopic coding with aniline provides several benefits. By introducing a hydrophobic moiety into hydrophilic molecules, hydrophobicity is increased, facilitating both reverse phase separation and ESI-MS detection. Moreover, the different labeling patterns for aldose sugars and ketose sugars simplify their separation. In vitro isotopic coding provides additional criterion for the identification of metabolites in complex matrices by producing an easily recognizable doublet ion pattern. Even though in vivo isotope coding can also be used (Lu et al., *J Am Soc Mass Spectrom* 2006, 17:37-50), it is not possible to control the chemical nature of the appended labeling agent. Being able to add hydrophobicity during isotope coding was a great analytical asset. The labeling also offers an opportunity to accurately quantify metabolites by MS, which is usually difficult if their $^{13}$C$_6$-coded standards are not available. This approach opens a door for comparative quantification of multiple analytes in a single run. In some studies, it is likely that one would compare the concentration of metabolites in a sample under one set of biological conditions with concentration found under another set of conditions. It can be simply done by labeling two samples with $^{13}$C$_6$-coded and non-$^{13}$C$_6$-coded aniline, respectively, and then two labeled samples are mixed equally. By MS, two labeled samples can be visually and quantitatively compared.

Example II

Identification of Unknown Metabolites in Complex Samples

Figure 7:
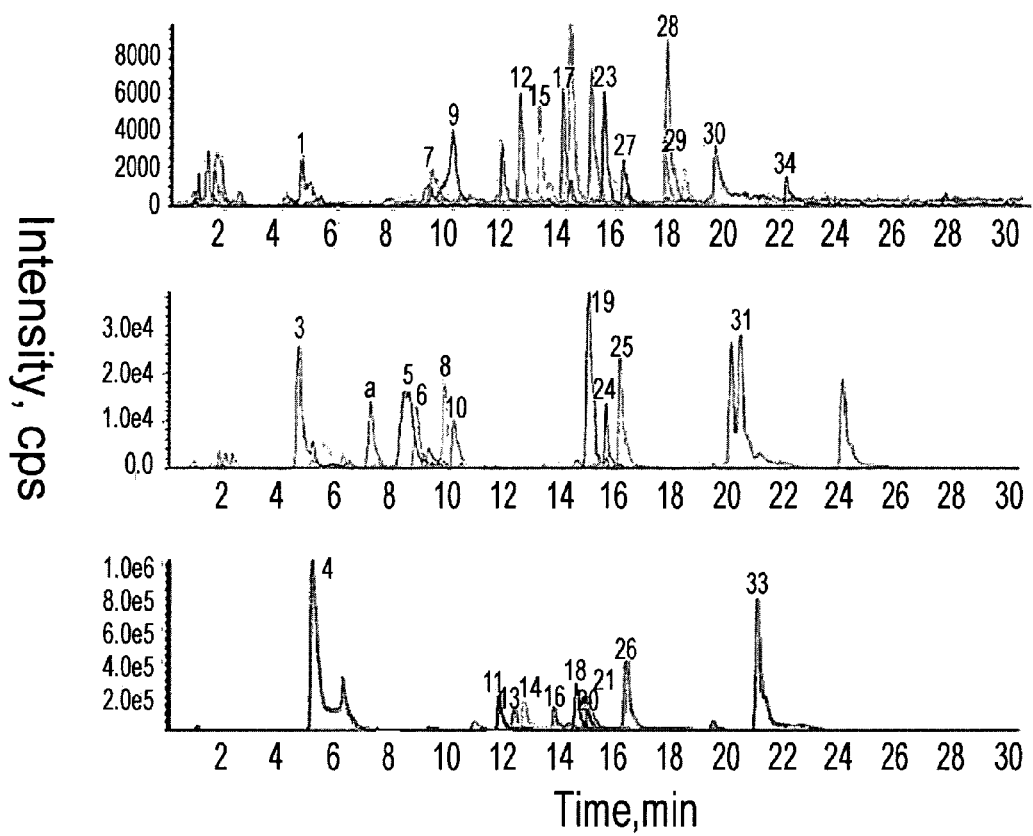
FIG. 7 shows overlapped extracted ion chromatograms of metabolites identified from yeast extract. Peak identification is given in Table 3. Peak "a" is identified as of D-6-phosphoglucono-δ-lactone without confirmation with a standard. LC-MS conditions are as described in Example I.

Cell extracts comprise a huge molecular pool with high possibilities that molecules with less than one mass unit difference are co-eluted, which cannot be distinguished by common MS. Thus reliance only on retention time and m/z value is not ensured for unique assignment of a metabolite. To increase the identification reliability, we set up another criterion of in vitro $^{13}$C labeling. Two aliquots of same cell extract solution were simultaneously labeled with aniline and aniline-$^{13}$C$_6$, respectively, and mixed at 1:1 ratio. Anything which was labeled in this mixture will generate two derivatives, which will completely co-elute. Accordingly, MS spectrum for this peak should have a doublet with mass difference of 6.0×n (n=1, 2, 3). A search was performed first by m/z value, and the returned peaks were further examined by retention time and MS doublet. The found metabolite peaks are reconstructed in FIG. 7, which is separated in 3 panes based on peak intensities. We do not have standards for D-6-phospho-glucono-δ-lactone, but a peak was found by its m/z searching, and the retention time is also reasonable. We assume this peak is this metabolite. Xylulose-5-phosphate and 2-phosphoglycerate are also not available; searching for their m/z did not return any reasonable peaks. Theoretically, the labeling should detect these molecules and we assume they exist at undetectable concentrations. This is also true for ribose-5-phosphate, which was not detected even though the standard has good detection sensitivity. Remarkably, except for these few intermediates, all other intermediates, nucleotides and coenzymes involved in central carbon metabolism are found.

Example III

Global Relative Quantification

Control and experimental samples are derivatized separately with the $^{12}$C- and $^{13}$C-isoforms of aniline, and the two samples mixed at 1:1 ratio. After LC-MS analysis, the concentrations of individual metabolites are determined from the ratio between intensity of corresponding light (sample 1) and heavy (sample 2) peaks (e.g. metabolites at the same concentration in the two samples will appear in a 1:1 isotope ratio. It has been shown in proteomics that there is a linear relationship between isotope ratio and relative concentration spanning more than $10^3$ in relative concentration.

Example IV

Analysis of Ganoderic Acids in Mushroom Extracts

Synthesis of 3-carbinol-1-methylpyridinium iodide (CMP) and 3-carbinol-1-methyl-$d_3$-pyridinium iodide (CMP-$d_3$) was carried out as follows: 50 mmol of iodomethane (-$d_0$ or -$d_3$) was added to 2-bromopyridine (10 mmol, 0.97 ml) or 3-carbinolpyridine (10 mmol, 0.96 ml) and solution was stirred at room temperature for 1 hour. Resulting crystals were washed with cold acetone and dried in vacuum.

ReishiMax mushroom extracts were used to examine the capability of the GSIST for tentative identification of ganoderic acids. Aliquots of sample were split into the two aliquots and each aliquot was individually derivatized with CMP (light) and CMP-$d_3$ (heavy) form of labeling reagent. After derivatization, the aliquots were combined and analyzed using LC-MS. Visual examination chromatograms showed that most of the high intensity peaks were potentially derivatized ganoderic acids. For detailed analysis we used a rule in which two ions with a mass difference of n×3 amu corresponding to CMP (light) and CMP-$d_3$ (heavy) derivatives must be found to co-elute in chromatogram (n represents the number of the derivatizing tags per labeled molecule and 3 amu is molecular weight difference between CMP and CMP-$d_3$ tags). Ganoderic acids were then identified as follows. It was assumed that all ganoderic acids contain only one carboxyl group and difference between co-eluting ions must be 3 amu (doublet). The ratio of ion intensities of corresponding doublets must be in the range of 0.8-1.2. Molecular mass of the original (underivatized) compound was calculated from the molecular mass of the ion found in the MS scan by subtracting the molecular mass of the derivatizing tag. These calculated molecular masses were then used to search a carboxyl group containing-ganoderic acid database. Multiple-carboxyl group-containing compounds and doublets outside defined range of ratios were excluded from the list obtained.

TABLE 3

Ganoderic acid identification results.

| Peak # | m/z | RT [min] | Ratio | Match | Compound |
|---|---|---|---|---|---|
| 1 | 509.24 | 18.71 | −1.04 | ND | |
| 2 | 514.24 | 3.44 | 1.19 | ND | |
| 3 | 516.29 | 15.79 | 1.11 | ND | |
| 4 | 529.26 | 17.20 | −1.04 | ND | |
| 5 | 530.28 | 17.13 | 1.12 | ND | |
| 6 | 547.28 | 8.32 | −1.03 | ND | |
| 7 | 552.35 | 14.76 | −1.04 | T | Lucidenic Acid H |
| 8 | 553.27 | 18.94 | 1.01 | ND | |
| 9 | 553.30 | 12.42 | 1.29 | ND | |
| 10 | 558.37 | 18.52 | 1.03 | T | Ganoderic Acid S1 |
| 11 | 562.30 | 14.11 | 1.06 | T | Lucidenic Acid D1 |
| 12 | 564.32 | 14.72 | 1.04 | ND | |
| 13 | 564.32 | 13.01 | −1.04 | T | Lucidenic Acid D |
| 14 | 565.32 | 13.00 | 1.10 | ND | |
| 15 | 566.32 | 4.39 | 1.21 | T | Lucidenic Acid B Lucidenic Acid E1 Lucidenic Acid L |
| 16 | 566.33 | 7.22 | −1.07 | T | Methyl Lucidenate G |
| 17 | 586.36 | 17.37 | −1.26 | ND | |
| 18 | 588.52 | 26.93 | −1.18 | ND | |
| 19 | 596.30 | 3.57 | −1.21 | ND | |
| 20 | 598.32 | 3.37 | 1.08 | ND | |
| 21 | 604.52 | 25.79 | −1.01 | ND | |
| 22 | 606.36 | 14.81 | 1.00 | ND | |
| 23 | 616.37 | 4.35 | −1.25 | ND | |
| 24 | 622.36 | 13.33 | 1.25 | S | Ganoderic Acid A |
| 25 | 632.31 | 15.15 | −1.00 | T | Ganosporeric Acid |
| 26 | 638.35 | 4.89 | 1.18 | ND | |
| 27 | 639.35 | 4.79 | 1.20 | ND | |
| 28 | 644.40 | 15.16 | 1.18 | ND | |
| 29 | 650.34 | 14.84 | 1.10 | ND | |
| 30 | 651.35 | 14.76 | 1.03 | ND | |
| 31 | 663.55 | 28.35 | 1.03 | ND | |
| 32 | 669.34 | 6.74 | −1.20 | ND | |
| 33 | 676.33 | 15.13 | 1.03 | S | Ganoderic Acid F |
| 34 | 678.35 | 13.81 | 1.09 | S | Ganoderic Acid H |
| 35 | 694.34 | 8.40 | −1.02 | ND | |
| 36 | 708.32 | 15.27 | 1.16 | T | Ganoderic Acid Mh |
| 37 | 710.34 | 15.03 | 1.29 | ND | |
| 38 | 715.40 | 12.86 | 1.30 | ND | |
| 39 | 715.55 | 27.94 | 1.04 | ND | |
| 40 | 722.34 | 14.76 | −1.15 | ND | |
| 41 | 738.36 | 13.40 | −1.12 | ND | |
| 42 | 738.36 | 14.18 | −1.14 | ND | |
| 43 | 764.34 | 15.59 | 1.13 | ND | |
| 44 | 766.36 | 15.45 | 1.20 | ND | |
| 45 | 794.35 | 14.40 | −1.20 | ND | |
| 46 | 795.36 | 14.33 | 1.13 | ND | |
| 47 | 818.59 | 24.96 | 1.03 | ND | |
| 48 | 1014.57 | 17.49 | −1.13 | ND | |
| 49 | 1025.47 | 19.81 | −1.03 | ND | |
| 50 | 1036.62 | 15.38 | −1.15 | ND | |
| 51 | 1047.57 | 16.08 | 1.15 | ND | |
| 52 | 1064.58 | 16.03 | −1.27 | ND | |
| 53 | 1089.59 | 16.44 | −1.13 | ND | |

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

The complete disclosures of all patents, patent applications including provisional patent applications, and publications, and electronically available material (e.g., GenBank amino acid and nucleotide sequence submissions) cited herein are incorporated by reference. The foregoing detailed description and examples have been provided for clarity of understanding only. No unnecessary limitations are to be understood therefrom. The invention is not limited to the exact details shown and described; many variations will be apparent to one skilled in the art and are intended to be included within the invention defined by the claims.

What is claimed is:

1. A method for identifying or quantifying a plurality of small molecule analytes, the method comprising:
    providing a control sample comprising known quantities of a plurality of small molecule analytes, each analyte comprising a different reactive functional group;
    providing an experimental sample comprising a plurality of said small molecule analytes;
    dividing the experimental sample into first and second experimental subsamples;
    adding an amount of the control sample to the first experimental subsample;
    contacting a first isotopic variant of a labeling reagent with each said analyte in the control sample to yield a plurality of first isotopically labeled analytes, wherein the labeling reagent is covalently linked to the analytes at the different reactive functional groups;
    contacting a second isotopic variant of the labeling reagent with each said analyte in each of the first and second experimental subsamples to yield first and second experimental subsamples each comprising a plurality of second isotopically labeled analytes, wherein the first and second isotopically labeled analytes are chemically equivalent yet isotopically distinct;
    adding equal amounts of the control sample to each of the first and second experimental subsamples to yield first and second combined samples;
    subjecting each of the first and second combined samples to mass spectrometric analysis; and
    comparing peak intensities generated by the first and second combined samples to identify or quantify the plurality of analytes in the experimental sample.

2. The method of claim 1 further comprising subjecting the samples to fractionation prior to mass spectrometric analysis.

3. The method of claim 1 wherein the labeling reagent comprises an amine.

4. The method of claim 3 wherein the labeling reagent further comprises a hydrophobic moiety.

5. The method of claim 4 wherein the labeling reagent is aniline or an aniline derivative.

6. The method of claim 1 wherein the reactive functional groups comprise a functional group selected from the group consisting of a carbonyl, phosphate and carboxyl.

7. The method of claim 6 wherein the reactive function groups comprise carbonyl, phosphate and carboxyl.

8. The method of claim 1 wherein the small molecule analytes comprise primary or secondary cellular metabolites.

* * * * *